US012233180B2

(12) United States Patent
Jinadatha

(10) Patent No.: US 12,233,180 B2
(45) Date of Patent: Feb. 25, 2025

(54) METHODS FOR ORGANIZING THE DISINFECTION OF ONE OR MORE ITEMS CONTAMINATED WITH BIOLOGICAL AGENTS

(71) Applicant: The United States Government as represented by the Department of Veterans Affairs, Washington, DC (US)

(72) Inventor: Chetan Jinadatha, Temple, TX (US)

(73) Assignee: The United States Government as represented by the Department of Veterans Affairs, Washington, DC (US)

(*) Notice: Subject to any disclaimer, the term of this patent is extended or adjusted under 35 U.S.C. 154(b) by 151 days.

(21) Appl. No.: 17/892,018

(22) Filed: Aug. 19, 2022

(65) Prior Publication Data
US 2022/0387650 A1 Dec. 8, 2022

Related U.S. Application Data

(63) Continuation of application No. 17/033,138, filed on Sep. 25, 2020, now Pat. No. 11,433,153, which is a
(Continued)

(51) Int. Cl.
*H04Q 5/22* (2006.01)
*A61L 2/24* (2006.01)
(Continued)

(52) U.S. Cl.
CPC ............ *A61L 2/24* (2013.01); *G06K 7/10118* (2013.01); *G06K 7/10415* (2013.01);
(Continued)

(58) Field of Classification Search
CPC ... A61L 2/24; A61L 2/10; A61L 2/208; A61L 2202/14; A61L 2202/25; G06K 7/10118;
(Continued)

(56) References Cited

U.S. PATENT DOCUMENTS 6,049,745 A 4/2000 Douglas et al.
6,657,543 B1 12/2003 Chung
(Continued)

FOREIGN PATENT DOCUMENTS

AU 2013296299 8/2013
AU 2019206017 8/2013
(Continued)

OTHER PUBLICATIONS

Block, S.S., Peroxygen compounds. In: Block S.S., ed., Disinfection, sterilization, and Preservation, Miler/6E04u Lippincott & Wilkins. 2001; 185-204.
(Continued)

*Primary Examiner* — Toan N Pham
(74) *Attorney, Agent, or Firm* — Ballard Spahr LLP

(57) ABSTRACT

The invention provides method for organizing the disinfection of one or more items contaminated with biological agent(s) comprising (a) attaching a radio-frequency ID (RFID) tag to an item(s) to be disinfected; exposing the item(s) of (a) to a disinfecting means for a period sufficient to disinfect the item; and (c) obtaining a signal from the tagged item when disinfection is complete thereby organizing the disinfection of one or more items.

19 Claims, 12 Drawing Sheets

Related U.S. Application Data continuation of application No. 16/289,539, filed on Feb. 28, 2019, now Pat. No. 10,824,825, which is a continuation of application No. 14/419,032, filed as application No. PCT/US2013/053307 on Aug. 1, 2013, now Pat. No. 10,255,466.

(60) Provisional application No. 61/678,558, filed on Aug. 1, 2012.

(51) Int. Cl.
| | |
|---|---|
| *G06K 7/10* | (2006.01) |
| *G06Q 50/22* | (2018.01) |
| *G16H 40/20* | (2018.01) |
| *G16H 40/63* | (2018.01) |
| *A61L 2/10* | (2006.01) |
| *A61L 2/20* | (2006.01) |

(52) U.S. Cl.
CPC ......... *G06K 7/10475* (2013.01); *G06Q 50/22* (2013.01); *G16H 40/20* (2018.01); *G16H 40/63* (2018.01); *A61L 2/10* (2013.01); *A61L 2/208* (2013.01); *A61L 2202/14* (2013.01); *A61L 2202/25* (2013.01); *Y02A 90/10* (2018.01)

(58) Field of Classification Search
CPC ........... G06K 7/10415; G06K 7/10475; G06Q 50/22; G16H 40/20; G16H 40/63; Y02A 90/10

See application file for complete search history.

(56) References Cited

U.S. PATENT DOCUMENTS

| | | | |
|---|---|---|---|
| 6,665,193 B1 | 12/2003 | Chung et al. | |
| 6,696,954 B2 | 2/2004 | Chung | |
| 6,703,935 B1 | 3/2004 | Chung et al. | |
| 6,883,710 B2 | 4/2005 | Chung | |
| 6,943,688 B2 | 9/2005 | Chung et al. | |
| 6,961,000 B2 | 11/2005 | Chung | |
| 6,973,716 B2 | 12/2005 | Chung et al. | |
| 7,036,729 B2 | 5/2006 | Chung | |
| 7,098,793 B2 | 8/2006 | Chung | |
| 7,154,046 B2 | 12/2006 | Chung | |
| 7,158,030 B2 | 1/2007 | Chung | |
| 7,168,030 B2 | 1/2007 | Ariyoshi | |
| 7,319,397 B2 | 1/2008 | Chung et al. | |
| 7,342,497 B2 | 3/2008 | Chung et al. | |
| 7,382,255 B2 | 6/2008 | Chung | |
| 7,423,535 B2 | 9/2008 | Chung et al. | |
| 7,492,258 B1 | 2/2009 | Shoarinejad et al. | |
| 7,877,166 B2 | 1/2011 | Harwig et al. | |
| 8,029,740 B2 * | 10/2011 | Hyde .................... | E05B 1/0069 422/301 |
| 8,114,346 B2 * | 2/2012 | Hyde .................... | E05B 1/0069 422/292 |
| 8,178,042 B2 | 5/2012 | Jung et al. | |
| 8,416,072 B2 | 4/2013 | Tenarvitz | |
| 10,255,466 B2 | 4/2019 | Jinadatha | |
| 2005/0134461 A1 | 6/2005 | Gelbman et al. | |
| 2005/0148819 A1 | 7/2005 | Noguchi et al. | |
| 2005/0246094 A1 | 11/2005 | Moscatiello | |
| 2005/0276889 A1 | 12/2005 | Yuan et al. | |
| 2006/0017659 A1 | 1/2006 | Ogawa et al. | |
| 2006/0145865 A1 | 7/2006 | Forster | |
| 2006/0240563 A1 | 10/2006 | Kippenhan et al. | |
| 2007/0094303 A1 | 4/2007 | Zwingenberger et al. | |
| 2007/0139202 A1 | 6/2007 | Austin | |
| 2007/0202005 A1 | 8/2007 | Maschke | |
| 2008/0056933 A1 | 3/2008 | Moore et al. | |
| 2008/0095661 A1 * | 4/2008 | Kohler .................... | C02F 1/325 422/119 |
| 2008/0131332 A1 | 6/2008 | Nguyen et al. | |
| 2008/0265179 A1 * | 10/2008 | Havens .................... | A61L 2/10 250/492.1 |
| 2009/0035189 A1 | 2/2009 | Wu et al. | |
| 2009/0198371 A1 | 8/2009 | Emanuel et al. | |
| 2010/0155339 A1 * | 6/2010 | Gunter .................... | C02F 1/325 210/85 |
| 2010/0171586 A1 | 7/2010 | Park et al. | |
| 2010/0295943 A1 | 11/2010 | Cha et al. | |
| 2011/0104005 A1 | 5/2011 | Da Rocha Costa | |
| 2012/0073614 A1 | 3/2012 | Otani et al. | |
| 2012/0313014 A1 | 12/2012 | Stibich et al. | |
| 2012/0313532 A1 | 12/2012 | Stibich et al. | |
| 2013/0002445 A1 | 1/2013 | Stibich et al. | |
| 2013/0277574 A1 | 10/2013 | Dayton | |
| 2013/0330235 A1 | 12/2013 | Stibich et al. | |
| 2014/0322183 A1 | 10/2014 | Milone et al. | |
| 2015/0205985 A1 | 7/2015 | Jinadatha | |

FOREIGN PATENT DOCUMENTS

| | | |
|---|---|---|
| AU | 2017204657 | 7/2017 |
| CA | 2880536 | 2/2014 |
| CA | 3086557 | 7/2020 |
| CN | 101496072 A | 7/2009 |
| CN | 201300516837 | 8/2013 |
| CN | 201810568509.4 | 8/2013 |
| CN | 103483452 A | 1/2014 |
| CN | 103483453 A | 1/2014 |
| EP | 2504822 A1 | 10/2012 |
| EP | 13825140.0 | 2/2015 |
| WO | WO 2007/073464 | 6/2007 |
| WO | WO-2007/073476 A2 | 6/2007 |
| WO | WO-2010/042849 A1 | 4/2010 |
| WO | WO 2012/033850 | 3/2012 |
| WO | WO-2012/037192 A1 | 3/2012 |
| WO | WO-2013/106077 A2 | 7/2013 |
| WO | PCT/US2013/053307 | 8/2013 |
| WO | WO-2014/039076 A1 | 3/2014 |

OTHER PUBLICATIONS

Boyce, J.M. et al., Terminal—Decontamination of Patient Rooms Using an Automated UV Light. ICHE. 2011; 32(8):737-42.

Carling, P.C. et al., Identifying Opportunities to Enhance Environmental Cleaning in 23 Acute Care Hospitals. ICHE. 2008; 29(1):1-7.

Centers for Disease Control and Prevention, *Pseudomonas aeruginosa* Infections Associated with Transrectal Ultrasound-guided Prostate Biopsies—Georgia, 2005. MMWR CDC Surveill Summ. 2006; 55:776-7.

Datta, R. et al., Environmental Cleaning Intervention and Risk of Acquiring Multidrug-Resistant Organisms from Prior Room Occupants. Arch Intern Med. 2011; 171(6):491-4.

Holmdahl, T. et al., A Head-to-Head Comparison of Hydrogen Peroxide Vapor and Aerosol Room Decontamination Systems. ICHE. 2011; 32(9):831-6.

Lowry, P.W. et al., *Mycobacterium chelonae* Causing Otitis Media in an Ear-Nose-and-Throat Practice. N Engl J Med. 1988; 319:978-82.

McCarthy, G.M. et al., Infection Control Practices Across Canada: Do Dentists Follow the Recommendations? J Can Dent Assoc. 1999; 65:506-11.

Mehta, A.C. et al., Prevention of Flexible Bronchoscopy-Associated Infection. Chest. 2006; 128:1742-55.

Meyers, H. et al., An Outbreak of *Mycobacterium chelonae* Infection Following Liposuction. Clin Infect Dis. 2002; 34:1500-7.

Morgan, D.J. et al., Transfer of Multidrug-Resistant Bacteria to Healthcare Workers' Gloves and Gowns After Patient Contact Increases with Environmental Contamination. Crit Care Med. 2012; 40(4):1045-51.

Otter, J.A. et al., The Role Played by Contaminated Surfaces in the Transmission of Nosocomial Pathogens. ICHE. 2011; 32(7):687-99.

Parvez, N. et al., Universal MRSA Nasal Surveillance: Characterization of Outcomes at a Tertiary Care Center and Implications for Infection Control. South Med J. 2010; 103(11):1084-91.

(56) References Cited

OTHER PUBLICATIONS

Reusable Electronic Baggage Tag Powered by RFID by Swedberg Oct. 6, 2010.
Rutala, W.A. and Weber, D.J., Are Room Decontamination Units Needed to Prevent Transmission of Environmental Pathogens? Infect Control Hosp Epidermiol. 2011; 32(8):743-7.
Rutala, W.A. et al., Rapid Hospital Room Disinfection Using Ultraviolet (UV) Light with a Nanostructured UV-Reflective Wall Coating. Infect Control Hosp Epidermiol. 2013; 34(5):527-9.
Rutala, W.A. et al., Room Decontamination with UV Radiation. Infect Control Hosp Epidermiol. 2010; 31(10):1025-9.
Saint Michael's Medical Center Adopts IBM Sensor Technology for Tracking Medical Equipment IBM News room—2010-1041-09.
Spach, D.H. et al., Transmission of Infection by Gastrointestinal Endoscopy and Bronchoscopy. Ann Intern Med. 1993; 118:117-28.
Stibich, M. et al., Evaluation of a Pulsed-Xenon Ultraviolet Room Disinfection Device for Impact on Hospital Operations and Microbial Reduction. Infect Control Hosp Epidermiol. 2011; 32(3):286-8.
Turner, F.J., Hydrogen peroxide and other oxidant disinfectants. In: Block SS, ed. Disinfection sterilization, and preservation. Philadelphia: Lea & Febiger. 1983:240-50.
Weber, D.J. and Rutala, W.A., Lessons from Outbreaks Associated with Bronchoscopy. Infect Control Hosp Epidermiol. 2001; 22:403-8.
Zaidi, M. et al., Disinfection and sterilization practices in Mexico. J Hosp Infect. 1995; 31:25-32.
Supplementary Partial European Search Report issued on Mar. 1, 2016 by the European Patent Office for Patent Application No. 13825140.0, which was filed on Aug. 1, 2013 and published as EP 2879721 on Jun. 10, 2015 (Inventor—Chetan Jinadatha; Applicant—United States of America as Represented by the Department of Veteran's Affairs) (7 pages).
Supplementary European Search Report and Written Opinion issued on Jul. 11, 2016 by the European Patent Office for Patent Application No. 13825140.0, which was filed on Aug. 1, 2013 and published as EP 2879721 on Jun. 10, 2015 (Inventor—Chetan Jinadatha; Applicant—United States of America as Represented by the Department of Veteran's Affairs) (8 pages).
International Search Report and Written Opinion mailed on Nov. 13, 2013 by the International Searching Authority for Patent Application No. PCT/US2013/053307, which was filed on Aug. 1, 2013 and published as WO 2014/022717 on Feb. 6, 2014 (Inventor—Chetan Jinadatha; Applicant—United States of America as Represented by the Department of Veteran's Affairs) (9 pages).
International Preliminary report on Patentability issued on Feb. 3, 2015 by the International Searching Authority for Patent Application No. PCT/US2013/053307, which was filed on Aug. 1, 2013 and published as WO 2014/022717 on Feb. 6, 2014 (Inventor—Chetan Jinadatha; Applicant—United States of America as Represented by the Department of Veteran's Affairs) (7 pages).
Examination Report was issued on Jul. 19, 2018 by the Australian Patent Office for AU Application No. 2017204657, filed on Jul. 7, 2017 and published as AU 2017204657 on Jul. 20, 2017 (Applicant—The United States of America as represented by the Department of Veterans Affairs) (5 Pages).
Examination Report was issued on May 10, 2019 by the Australian Patent Office for AU Application No. 2017204657, filed on Jul. 7, 2017 and published as AU 2017204657 on Jul. 20, 2017 (Applicant—The United States of America as represented by the Department of Veterans Affairs) (6 Pages).
Office Action was issued on Jul. 17, 2020 by the Australian Patent Office for Application No. 2019206017, filed on Jul. 16, 2019 (8 Pages).
Non Final Rejection was issued on Feb. 17, 2016 by the USPTO for U.S. Appl. No. 14/419,032, filed Feb. 2, 2015 and granted as U.S. Pat. No. 10,255,466 on Apr. 9, 2019 (Inventor—Chetan Jinadatha) (9 Pages).
Response to Non Final Rejection was mailed on Aug. 17, 2017 to the USPTO for U.S. Appl. No. 14/419,032, filed Feb. 2, 2015 and granted as U.S. Pat. No. 10,255,466 on Apr. 9, 2019 (Inventor—Chetan Jinadatha) (20 Pages).
Final Rejection was issued on Oct. 2, 2017 by the USPTO for U.S. Appl. No. 14/419,032, filed Feb. 2, 2015 and granted as U.S. Pat. No. 10,255,466 on Apr. 9, 2019 (Inventor—Chetan Jinadatha) (31 Pages).
Response to Final Rejection and Request for Continued Examination was mailed on Apr. 2, 2018 to the USPTO for U.S. Appl. No. 14/419,032, filed Feb. 2, 2015 and granted as U.S. Pat. No. 10,255,466 on Apr. 9, 2019 (Inventor—Chetan Jinadatha) (49 Pages).
Non Final Rejection was issued on May 9, 2018 by the USPTO for U.S. Appl. No. 14/419,032, filed Feb. 2, 2015 and granted as U.S. Pat. No. 10,255,466 on Apr. 9, 2019 (Inventor—Chetan Jinadatha) (28 Pages).
Response to Non Final Rejection was mailed on Oct. 9, 2018 to the USPTO for U.S. Appl. No. 14/419,032, filed Feb. 2, 2015 and granted as U.S. Pat. No. 10,255,466 on Apr. 9, 2019 (Inventor—Chetan Jinadatha) (44 Pages).
Notice of Allowance was issued on Nov. 30, 2018 by the USPTO for U.S. Appl. No. 14/419,032, filed Feb. 2, 2015 and granted as U.S. Pat. No. 10,255,466 on Apr. 9, 2019 (Inventor—Chetan Jinadatha) (8 Pages).
Amendment to Notice of Allowance(Rule 312) was issued on Feb. 27, 2019 by the USPTO for U.S. Appl. No. 14/419,032, filed Feb. 2, 2015 and granted as U.S. Pat. No. 10,255,466 on Apr. 9, 2019 (Inventor—Chetan Jinadatha) (1 Page).
Notice of Allowance was issued on Mar. 11, 2019 by the USPTO for U.S. Appl. No. 14/419,032, filed Feb. 2, 2015 and granted as U.S. Pat. No. 10,255,466 on Apr. 9, 2019 (Inventor—Chetan Jinadatha) (2 Pages).
Issue Notification was issued on Mar. 20, 2019 by the USPTO for U.S. Appl. No. 14/419,032, filed Feb. 2, 2015 and granted as U.S. Pat. No. 10,255,466 on Apr. 9, 2019 (Inventor—Chetan Jinadatha) (1 Page).
Office Action was issued on Apr. 10, 2020 by the Chinese Patent Office for Application No. 201801568509.4, filed on Aug. 1, 2013, and published as CN109091686A on Dec. 28, 2018 (Inventor—Chetan Jinadatha) (12 Pages).
Office Action was issued on Dec. 2, 2020 by the Chinese Patent Office for Application No. 201801568509.4, filed on Aug. 1, 2013, and published as CN109091686A on Dec. 28, 2018 (Inventor—Chetan Jinadatha) (10 Pages).
Non Final Rejection was issued on Feb. 19, 20 by the USPTO for U.S. Appl. No. 16/289,539, filed Feb. 28, 2019 and granted as U.S. Pat. No. 10,824,825 on Nov. 3, 2020 (Inventor—Chetan Jinadatha) (6 Pages).
Response to Non Final Rejection was mailed on May 1, 2020 to the USPTO for U.S. Appl. No. 16/289,539, filed Feb. 28, 2019 and granted as U.S. Pat. No. 10,824,825 on Nov. 3, 2020 (Inventor—Chetan Jinadatha) (8 Pages).
Notice of Allowance was issued on Oct. 9, 2020 by the USPTO for U.S. Appl. No. 16/289,539, filed Feb. 28, 2019 and granted as U.S. Pat. No. 10,824,825 on Nov. 3, 2020 (Inventor—Chetan Jinadatha) (2 Pages).
Issue Notification was issued on Oct. 14, 2020 by the USPTO for U.S. Appl. No. 16/289,539, filed Feb. 28, 2019 and granted as U.S. Pat. No. 10,824,825 on Nov. 3, 2020 (Inventor—Chetan Jinadatha) (1 Page).
U.S. Appl. No. 61/678,558, filed Aug. 1, 2012, Chetan Jinadatha (U.S. Dept. of Veterans Affairs).
U.S. Appl. No. 14/419,032 (U.S. Pat. No. 10,255,466), filed Feb. 2, 2015 (Apr. 9, 2019), Chetan Jinadatha (U.S. Dept. of Veterans Affairs).
U.S. Appl. No. 16/289,539 (U.S. Pat. No. 10,824,825), filed Feb. 28, 2019 (Nov. 3, 2020), Chetan Jinadatha (U.S. Dept. of Veterans Affairs).
U.S. Appl. No. 17/033,138 (U.S. Pat. No. 11,433,153), filed Sep. 25, 2020 (Sep. 6, 2022), Chetan Jinadatha (U.S. Dept. of Veterans Affairs).

(56) References Cited

OTHER PUBLICATIONS

Examination Report issued on Nov. 7, 2024 by the Canadian Patent Office for CA Application No. 3,086,557, filed on Aug. 1, 2013 (Applicant—The United State of America as represented by The Department of Veterans Affairs) (3 pages).

* cited by examiner

METHODS FOR ORGANIZING THE DISINFECTION OF ONE OR MORE ITEMS CONTAMINATED WITH BIOLOGICAL AGENTS

This Application is a continuation of U.S. application Ser. No. 17/033,138, filed on Sep. 25, 2020, which is a continuation of U.S. application Ser. No. 16/289,539, filed on Feb. 28, 2019, which is a continuation of U.S. application Ser. No. 14/419,032, filed on Feb. 2, 2015, which is a national stage filing under 35 U.S.C. § 371 of International Application No. PCT/US2013/053307, filed on Aug. 1, 2013, which claims the benefit of U.S. Provisional Application No. 61/678,558, filed on Aug. 1, 2012, the contents of which are herein incorporated by reference in their entireties.

Throughout this application various publications are referenced. The disclosures of these publications in their entireties are hereby incorporated by reference into this application in order to more fully describe the state of the art to which this invention pertains.

BACKGROUND OF THE INVENTION

Overview of Hospital Associated Infections

Hospital acquired or associated infections (HAI) are an important cause of mortality and morbidity affecting an estimated 1.7 million patients and causing 100,000 deaths annually in the United States.[1] As multiple drug resistant organisms (MDROs) represent an increasing challenge to successfully treat, they also significantly contribute to increasing health care costs,[2] not to mention unnecessary patient burden. Evidence suggests a 28-58% higher risk of infection is attributable to surface contamination and cross transmission, especially for Methicillin resistant *Staphylococcus aureus* (MRSA) and *Clostridium difficile* (*C. diff*).[3] Additionally, an estimated 20-40% of all HAI result from cross contamination via health care personnel either by direct patient contact or by touching contaminated environmental surfaces in the room to include reusable medical equipment's like IV poles, blood pressure cuffs, and monitors.[1] In addition to MRSA infections and *C. diff*, the role of environmental contamination for transmission has been studied in several other important infectious microbes including vancomycin resistant enterococcus (VRE), and *Acinetobacter baumanii*.[3,4] Contaminated surfaces contribute up to half of the risk for acquiring infections, as these organisms persist on environmental surfaces for many days. In the intensive care unit (ICU) setting, even improvements in cleaning visibly soiled surfaces can lead to reducing the rate of MRSA and VRE by 30-50%.[5,6] However, this requires an evaluation and feedback system that is quite labor intensive, and the sustainability of such costly efforts would undoubtedly be limited. In fact, several studies show that manual cleaning performed after patient rooms are vacated is unreliable, with residual contamination rates ranging up to 50%.[1-3] This residual environmental contamination with potentially resistant organisms endangers the health of the next room occupant, not to mention staff, and risks cross transmission throughout the hospital via hand transmission from health care workers as well as with reusable medical equipment. Even after appropriate room cleaning, patients subsequently admitted to rooms where MRSA, *C. diff* or VRE patients were previously isolated remain at increased risk from acquisition, due to environmental contamination. This has been well demonstrated in many prior studies where admission to a room previously occupied by an HAI-positive patient was associated with 28-58% increased risk of acquisition of these pathogens.[1-3] There have been multiple studies in various countries that have documented lack of compliance with established guidelines for disinfection leading to numerous outbreaks.[7-16]

How Current Cleaning Practices are Inadequate

Many HAI reduction initiatives, such as raising compliance of hand hygiene, antimicrobial stewardship programs and isolation/screening practices, have become standard practice. The environmental cleaning of patient rooms, however, has not evolved significantly in response to other HAI reduction efforts. Recent studies by Carling et al., demonstrate conclusively that manual cleaning is inadequate for effectively reducing the bio-burden in patient care areas because as many as 70% of high-touch surfaces (e.g., bed rails, call buttons, television remote controls) are missed, during both standard discharge and isolation cleanings.[17] This could also be applied to other reusable medical equipment that is present in the same patient room. This incomplete cleaning allows for organisms to remain on the room or equipment following patient discharge, placing the subsequent patient at a higher risk as organisms like MRSA, VRE and *C. diff* spores can survive in the environment from 3-12 months.[1]

The novel methods of the invention were devised to alleviate the aforementioned problems and should radically and systematically reduce the contamination on equipment or supplies and in-patient rooms.

SUMMARY OF THE INVENTION

Various embodiments described herein are directed to methods for organizing (manually or through automated means) the disinfection of one or more items contaminated with biological agent(s) comprising attaching a radio-frequency ID (RFID) tag to an item(s) to be disinfected, exposing the item(s) to a disinfecting means for a period sufficient to disinfect the item; and obtaining a signal from the tagged item when disinfection is complete thereby organizing the disinfection of one or more items.

The invention also provides methods for disinfection (manually or through automated means) of one or more items contaminated with biological agent(s) comprising exposing the item(s) having RFID tags to a disinfecting means for a period sufficient to disinfect the item and obtaining a signal from the tagged item(s) when disinfection is complete thereby organizing the process of disinfection of one or more items.

The invention also provides methods for detecting (manually or through automated means) whether an item exiting or leaving a designated space is contaminated comprising attaching a radio-frequency ID (RFID) tag to the item(s) to be disinfected, attaching an RFID to a chokepoint, and obtaining a signal from the tagged item indicating when a contaminated item crosses the chokepoint.

The invention further provides methods for detecting (manually or through automated means) whether an item exiting a designated space is clean or disinfected comprising attaching a radio-frequency ID (RFID) tag to the item(s) to be disinfected, attaching an RFID to a chokepoint, and obtaining a signal from the tagged item indicating when a clean or disinfected item crosses the chokepoint.

The invention also provides methods for organizing (manually or through automated means) the disinfection of a designated space contaminated with biological agent(s) comprising attaching one or more radio-frequency ID (RFID) tags to a designated area to be disinfected, exposing the designated area or portion thereof to a disinfecting means for a period sufficient to disinfect the designated area, and obtaining a signal from the tagged designated area when disinfection is complete thereby organizing the disinfection of the designated space.

The invention further provides methods for disinfection (manually or through automated means) of a designated space contaminated with biological agent(s) comprising exposing the designated space or portion thereof to a disinfecting means for a period sufficient to disinfect the designated space or portion thereof, said designated space or portion thereof having one or more radio-frequency ID (RFID) tags and obtaining a signal from the tagged designated space or portion thereof when disinfection is complete thereby organizing the disinfection of the designated space or portion thereof.

Additionally provided are apparatus and systems for use in the methods of this invention.

DETAILED DESCRIPTION OF THE INVENTION

Definitions

Figure 1:
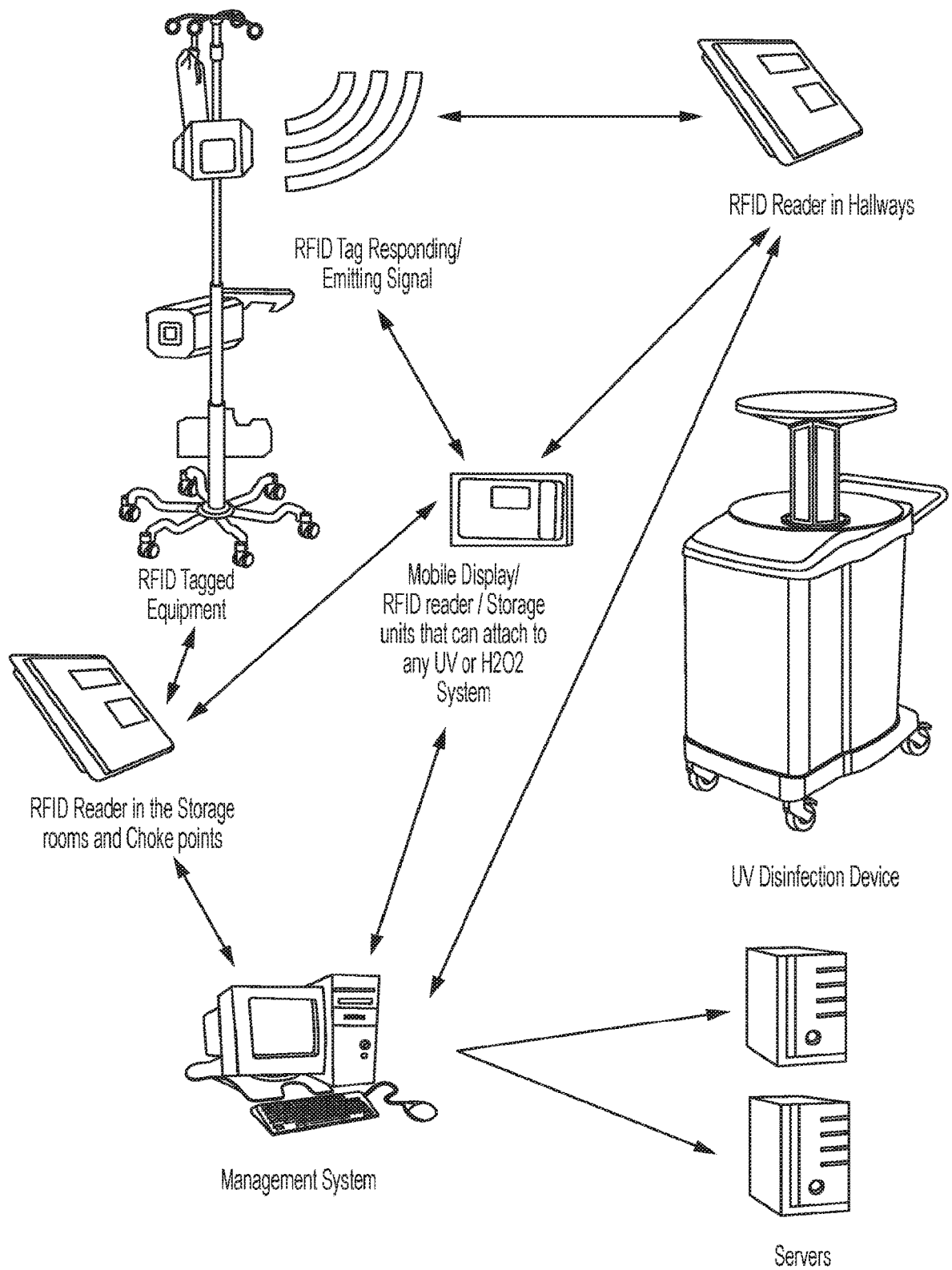
FIG. 1 is a diagram showing the process for disinfection of reusable medical equipment.

Healthcare associated/acquired infections (HAIs) or nosocomial infections are infections that may be acquired by a patient during the course of his/her hospital admission.

In accord with the practice of the invention, the disinfecting means may kill or inhibit biological contaminants including, but not limited to, micro-organisms, viral particles, fungal particles, spores to include *Clostridium difficile*, tuberculous particles, other infectious agents, microbes in human secretion, human excretion, dust and fecal material.

Patient room refers to a room occupied by a patient during his/her hospital stay.

Clean/Dirty utility or equipment room refers to a room used to store re-usable medical equipment such as IV poles, tray tables, wheelchairs, thermometer, console, computer on wheels (COW), blood pressure cuff/device, bedside commode, intravenous/infusion pump and pole (IV pole), SCD devices, cooling blankets, warming blankets (bear huggers), portable x-ray machines, equipment carts, monitors, various high dollar machines like Electroencephalograms (EEG), Electrocardiogram (EKG) machines, wheelchairs, walkers or crutches.

UV light refers to ultraviolet light delivered by, for example, the pulsed xenon lamp or mercury based technologies or equivalents at the appropriate frequency. The Mercury based technologies like Tru-D (Lumalier, TN) (FIG. 11) or V-360+ Room Sanitizer (UVDI, CA) uses a mercury lamp to produce UV light in the 254 nm range which is bactericidal. Pulsed xenon-UV germicidal irradiation produces a more broad-spectrum UV irradiation, but also produces large amounts of energy in the germicidal spectrum (200-320 nm) by using a xenon gas flash lamp (Xenex Healthcare Service, TX).

Hydrogen Peroxide refers to hydrogen peroxide dry mist, hydrogen peroxide vapor, vaporized Hydrogen peroxide, hydrogen peroxide fog or steam or spray or equivalent.

RFID refers to Radio-frequency Identification which is a wireless use of radio-frequency electromagnetic fields to transfer data for the purposes of identifying and/or tracking objects. There is no physical contact between communicating objects.

RFID tag/s refers to an object that can be applied, imbedded or otherwise attached onto a product, e.g., re-usable medical equipment or room entrance for the purposes of tracking the disinfection of equipment or patient rooms or utility storage rooms. These tags can be either active or passive or a hybrid thereof.

RFID reader/s also referred to as RFID interrogator refers to an object that contains a radio-frequency module, which transmits and/or receives radio-frequency signals. The reader's function is to interact with RFID tag(s). These readers can be either active or passive. They can also be fixed or mobile. Signals from the reader are further transmitted to either the mobile unit (also referred to here as Jangama) microprocessor or to the central data warehouse directly.

RFID system refers to the type of tag and reader used to track and interrogate objects. A Passive Reader Active Tag (PRAT) system includes a passive reader and a battery operated active tag wherein the reader only receives the signal from the active tags. An Active Reader Passive Tag (ARPT) system includes an active reader which transmits signals to the passive tags and also, optionally, receives signals from the passive tags. An Active Reader Active Tag (ARAT) system includes active tags that can respond to the interrogation from an active reader.

Fixed RFID readers used in this invention will be used near the entrance of re-usable medical equipment storage rooms or actual patient rooms which will allow for a highly defined reading area for when the tagged re-usable medical equipment go in and out of the storage area or patient room. Such readers could also function as choke point readers.

Mobile readers (which may be housed in a mobile unit, e.g., Jangama) in this invention may be used with the no-touch disinfection devices to alert environmental services staff of patient rooms or equipment in need of cleaning (also referred to herein as disinfecting) within an interrogation zone.

Cleaning includes terminally disinfecting a patient room after a patient has been discharged to keep it ready for the next patient. This refers to thoroughly disinfecting the patient bed; including the top, front, sides, headboard, side rails, mattress, between side rails; the nurse call light; the TV remote; all high touch surfaces such as tray tables, bedside tables and drawers, phone, armchairs, door handles, light switches, closet handles, etc.; disinfecting the bathroom to include the fixtures, support bars and other surfaces. Privacy curtains may be removed and bagged for laundry. Window curtains, ceilings and walls also may need to be disinfected. In cases where the occupant had, e.g., MRSA, C-Diff or VRE, the room may be terminally disinfected from floor to ceiling with agents such as diluted bleach. Additionally, all re-usable medical equipment in the room may be thoroughly cleaned or disinfected and returned to special processing department or the utility storage area. Cleaning may be generally done by the environmental services personnel in most hospitals and there is always a potential for missed opportunities, where a high touch area was not thoroughly cleaned per protocol. Such missed opportunities could result in HAI in patients or visitors. This is a tedious and time consuming process, thereby reducing the turnaround time for a patient room. The invention focuses on decreasing the room turnaround time by decreasing the time needed to terminally clean or disinfect the room and also electronically updating the availability of a room throughout the hospital system without relying on manual entry.

Re-usable medical equipment such as IV poles, wheelchairs, walkers, bedside commodes, etc. are used as needed. Between each patient use, this equipment may be stored in dirty equipment rooms and wheeled/transported to the special processing department where terminal cleaning of the equipment occurs per protocol. This also leads to a missed opportunity for cleaning, resulting in potential HAIs. This process also decreases the availability of re-usable medical devices during high patient census weeks and in ERs where efficiency is the key to delivering patient care. To address the issues, the invention in one embodiment, focuses on RFID tagged equipment which are held in storage rooms and disinfected with UV rays. The equipment will feature active RFID tags which can communicate with respective readers about its location, clean/unclean status, etc. The active tags would also enable the equipment to be tracked by a software/application on the hospital network making it easy for a nurse in emergency room trying to locate a clean/unused IV pole which could be on the med-surgical unit.

Figure 3:
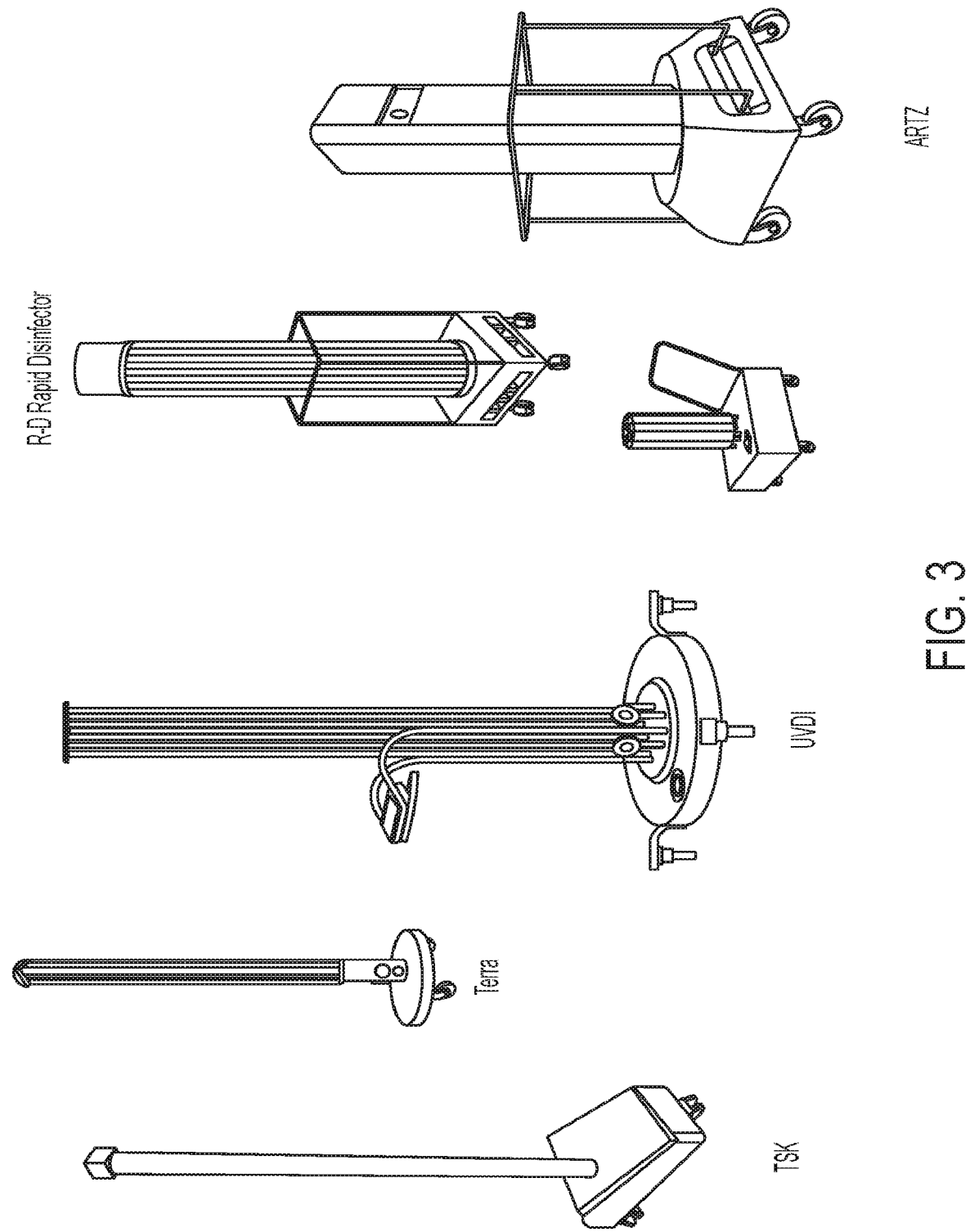
FIG. 3 shows photographs of the other Mercury-based UV disinfection machines.
Figure 4:
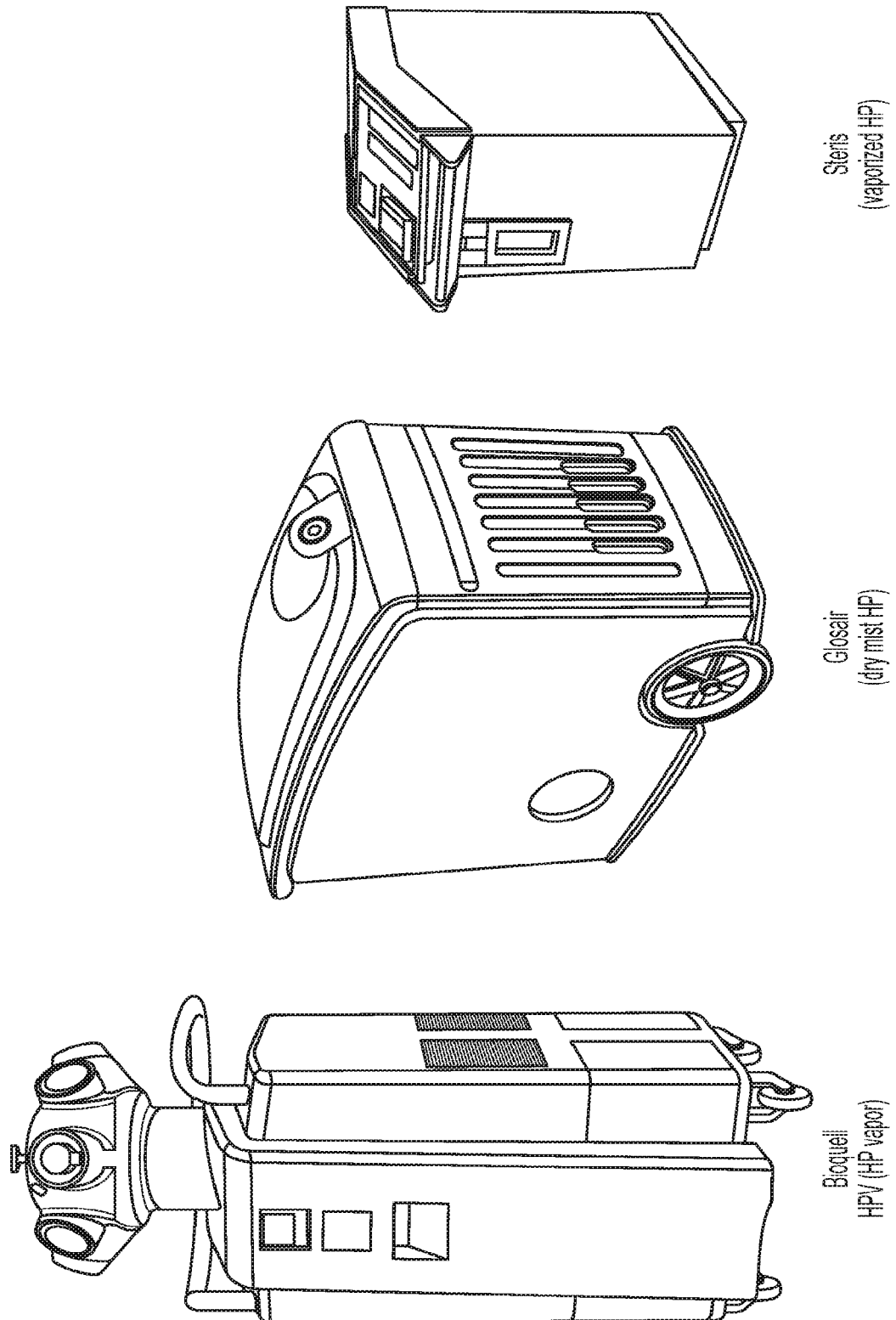
FIG. 4 shows photographs of the different Hydrogen Peroxide Systems.
Figure 8:
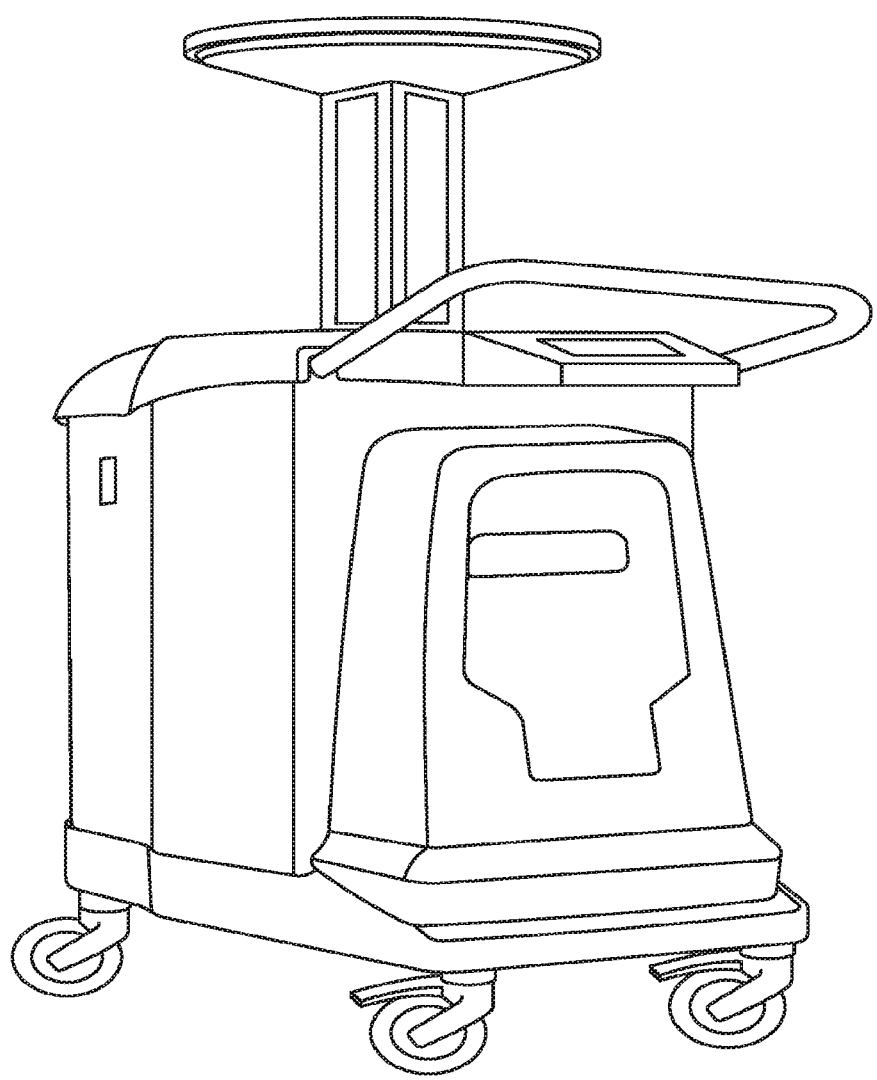
FIG. 8 shows drawing of a pulsed xenon UV device.

No touch disinfection systems are means of cleaning enclosed areas. The disinfection can be achieved either by using UV disinfection systems (either mercury-based as in FIG. 3 or 11 or pulsed-xenon-based as in FIG. 8) or hydrogen peroxide systems (vapor, mist or aerosolized as on FIG. 4). In either scenario, after manual cleaning, the device is placed in a room (typically discharged empty patient room) and run for a specified amount of time (disinfection cycle). For some devices, like a pulsed-xenon-based device, the device may have 2-4 positions of disinfection.

A chokepoint refers to a point of entry or escape, where a reader may be installed in order to track objects or to warn of the exit or entry of unclean equipment.

Figure 9:
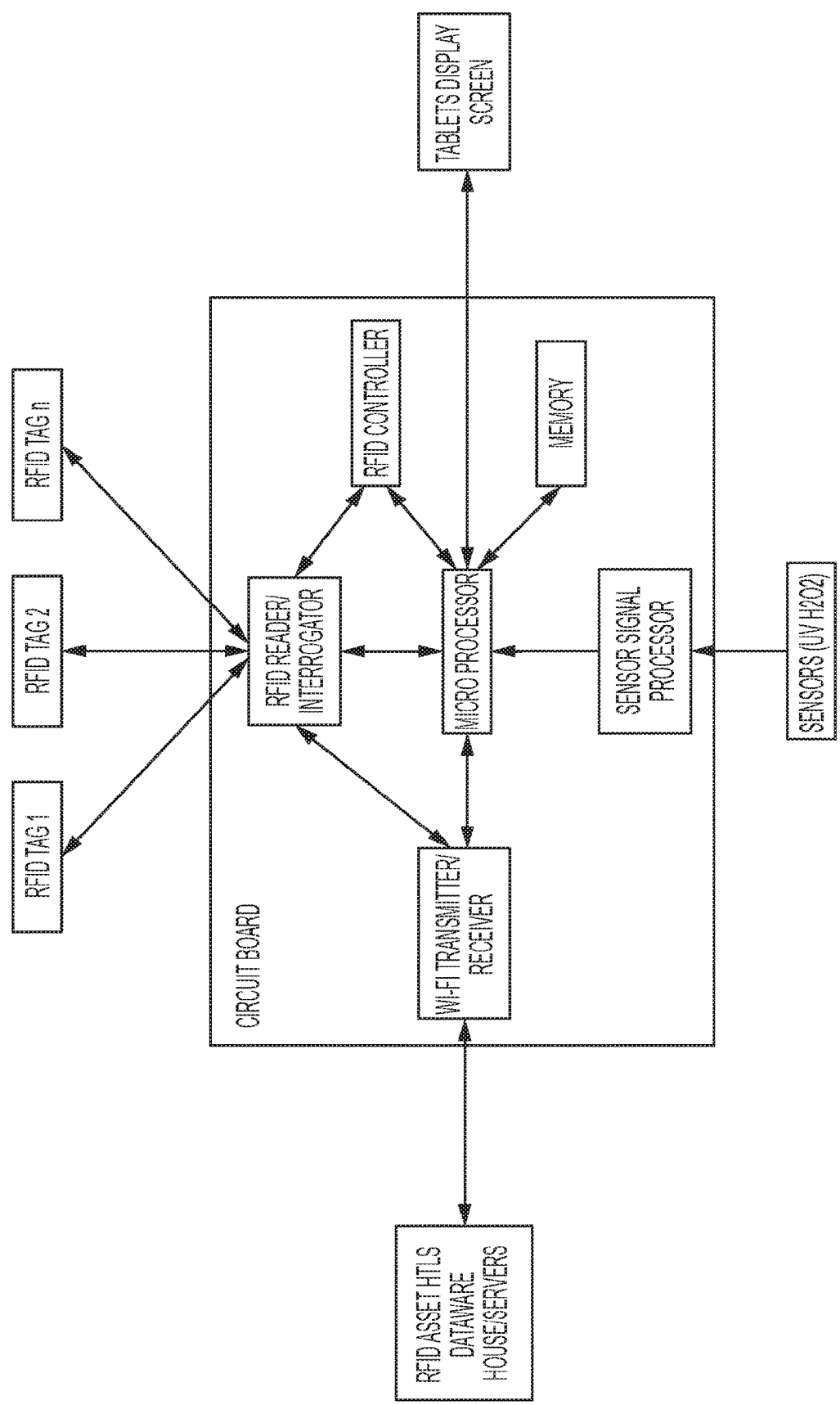
FIG. 9 shows an overall flow chart of the inner workings of the Jangama with optional memory feature.

A Jangama is a mobile or integrated unit to be used for organizing disinfection of rooms and equipment (FIG. 9).

As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a method comprising steps a, b, and c encompasses, for example, a method of performing steps in the order of steps a, c, and b, the order of steps c, b, and a, and the order of steps c, a, and b. Unless otherwise indicated, all numbers expressing quantities of ingredients, properties such as molecular weight, reaction conditions, and so forth as used herein, are to be understood as being modified in all instances by the term "about." Accordingly, unless indicated to the contrary, the numerical parameters herein are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

In order that the invention herein described may be more fully understood, the following description is set forth:

The invention provides methods for organizing the process of disinfection of one or more items contaminated with biological agent(s). The method comprises attaching a radio-frequency ID (RFID) tag to an item(s) to be disinfected. The method further comprises exposing the item(s) of (a) to a disinfecting means for a period sufficient to disinfect the item. Further, the method comprises obtaining a signal from the tagged item when disinfection is complete thereby organizing the disinfection of one or more items.

In one embodiment, the contaminated with biological agent(s) may be disinfected by the method of the invention.

The invention also provides methods for disinfection of one or more items contaminated with biological agent(s). The method comprises exposing the item(s) having RFID tags attached thereto or contained therein to a disinfecting means for a period sufficient to disinfect the item. The method further comprises obtaining a signal from the tagged item (e.g., via the RFID tag) when disinfection is complete.

In one embodiment, the method for organizing the disinfection of one or more items contaminated with biological agent(s) may be manual or an automated method. In another embodiment, the method for disinfection of one or more items contaminated with biological agent(s) may be manual or an automated method.

In one embodiment, the item to be disinfected is a device, machine or tool. The machine may be medical equipment, e.g., durable medical equipment or reusable medical equipment.

In an embodiment of the invention, the disinfecting means is a ultra-violet (UV) light system. In a further embodiment, the ultra-violet light is from pulsed xenon light. For example, disinfection systems are available that provide such pulsed light (Xenex Healthcare Services LLC) as shown in e.g. FIG. 8. In another example, the UV light may be from a mercury vapor UV lamp. In another example, the disinfection system may provide UV light such as Tru-D LLC's SmartUVC room disinfection system as shown in e.g. FIG. 11. The Mercury based technologies like Tru-D (Lumalier, TN) or V-360+ Room Sanitizer (UVDI, CA) uses a mercury lamp to produce UV light in the 254 nm range which is bactericidal.[18] Pulsed Xenon-UV germicidal irradiation produces a more broad-spectrum UV irradiation, but also produces large amounts of energy in the germicidal spectrum (200-320 nm) by using a xenon gas flash lamp (Xenex Healthcare Service, TX).[19]

Figure 2:
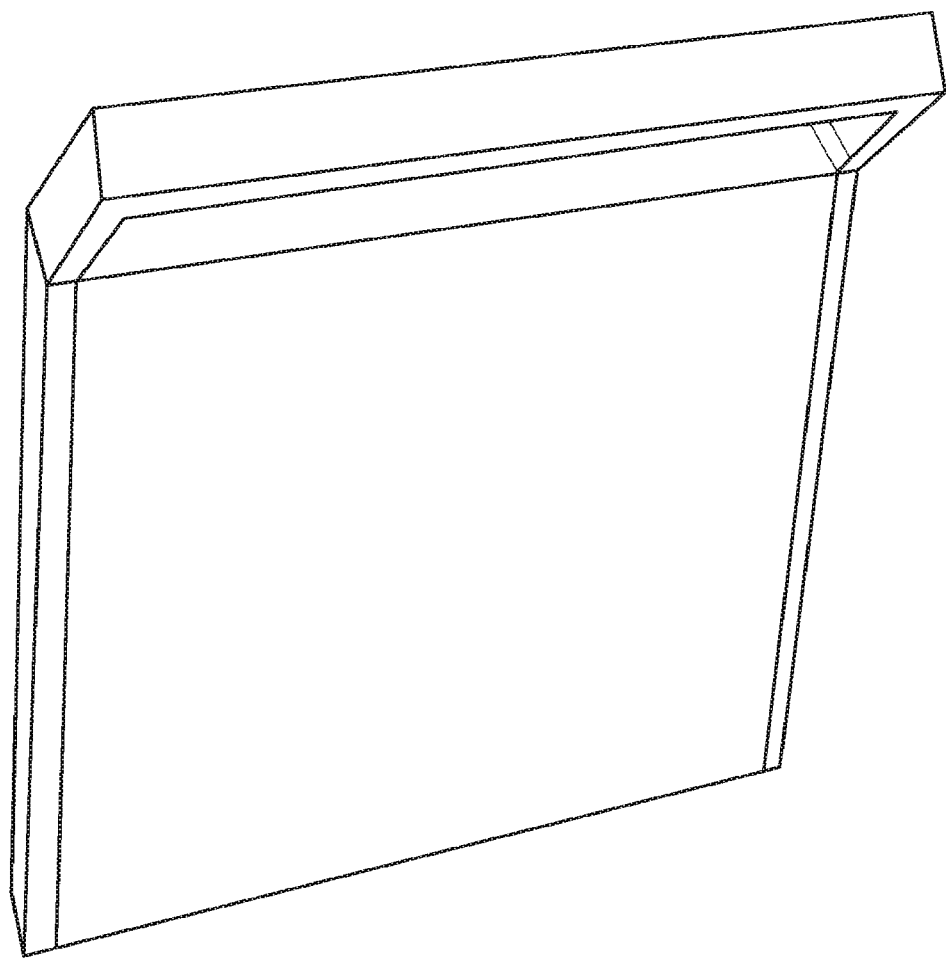
FIG. 2 is a photograph of a UV Aluminum reflector.

In accordance with the practice of the invention, the space or room where the equipment will be cleaned may be coated with a reflective coating (paint) (UVC 360, Lumacept, TN). This coating enhances reflectivity of the UVC, thus improving the overall disinfection and thoroughness of disinfection.[20] Additionally, the space or room to be cleaned may be lined with reflective aluminum panels with arching overheads as shown in e.g. FIG. 2. These panels enhance reflectivity of the UVC thus improving the overall disinfection and thoroughness of disinfection.

In a further embodiment, the disinfecting means may be a hydrogen peroxide system. Hydrogen peroxide systems may include hydrogen peroxide vapour (HPV), activated hydrogen peroxide, dry mist hydrogen peroxide or vaporized hydrogen peroxide.[21,22] Examples of hydrogen peroxide systems include, but are not limited to, Bioquell Aeration Units (Bioquell, UK), VHP ARD Biodecontamination System (Steris Corporation, OH), and GLOSAIR™ Healthcare Environmental Decontamination Systems (ASP Inc., CA) as shown in e.g. FIG. 4.

Examples of biological contaminants include, but are not limited to, micro-organisms, viral particles, fungal particles, spores to include *Clostridium difficile*, tuberculous particles, other infectious agents, microbes in human secretion, human excretion, dust and fecal material.

Further, the micro-organism may be a bacterium, fungus, protozoa, spore or virus. In another embodiment, the bacterium may be *Clostridium difficile, Clostridium botulinum*, or *Clostridium perfringens*, and its spores. Additionally, the bacterium may be a drug resistant bacterium. The drug resistant bacterium may be a methicillin-resistant *Staphylococcus aureus* (MRSA). Also, in another example, the bacterium may be *Staphylococcus epidermidis* or *Staphylococcus saprophyticus*. A further example of the drug resistant bacterium may be a Carbapenem-resistant gram-negative bacterium, or the gram negative bacteria *Hemophilus influenzae, Klebsiella pneumoniae*, or *Legionella pneumophila*. Additional examples of microorganisms include viruses such as human rhinovirus, poliovirus, norovirus, coxsackievirus or echovirus.

In one embodiment of the invention, the RFID tag may communicate with the disinfection means. In another embodiment, the RFID tag may communicate the initiation or completion of the cleaning or disinfection cycle to a computer. In a further embodiment, the method comprises processing the signal from the tagged item to create a log of the cleaning or disinfecting history of each RFID tagged item through a computer. In yet another embodiment, comprising processing the signal from the item(s) having an RFID tag to create a log of the cleaning or disinfecting history of each RFID tagged item through a computer.

The invention also provides methods for detecting whether an item exiting a designated space is contaminated. The method comprises attaching a radio-frequency ID (RFID) tag to the item(s) to be disinfected. The method further comprises attaching an RFID detector or reader to a chokepoint or transit point. Further, the method comprises obtaining a signal from the tagged item indicating when a contaminated item crosses the chokepoint or transit point.

In one embodiment, the method for detecting whether an item exiting a designated space is contaminated may be an automated method.

The invention further provides methods for detecting whether an item exiting a designated space is clean or disinfected. The method comprises attaching a radio-frequency ID (RFID) tag to the item(s) to be disinfected. The method further comprises attaching an RFID detector or reader to a chokepoint or transit point. Further, the method comprises obtaining a signal from the tagged item indicating when a clean or disinfected item crosses the chokepoint or transit point.

In one embodiment, the method for detecting whether an item exiting a designated space is clean or disinfected may be an automated method.

In accord with the practices of the invention, the method further comprises processing the signal from the tagged item to create a log of the RFID tagged item through a computer.

In a further embodiment, the RFID tag permits the creation of a log of the cleaning or disinfecting history of each RFID tagged item through a computer. In another embodiment, the RFID tag is connected to a chokepoint, and may provide notification when a piece of dirty equipment crosses the chokepoint. In another embodiment, the alert and notification system may be computer based, wherein a signal is sent to the data warehouse and appropriate personnel may be notified via cellphone, pager, or other means of communication, include any vibrating or flashing wireless device. In another embodiment, the notification device may be located on the door or other chokepoint itself and may be audible or visual.

Figure 5:
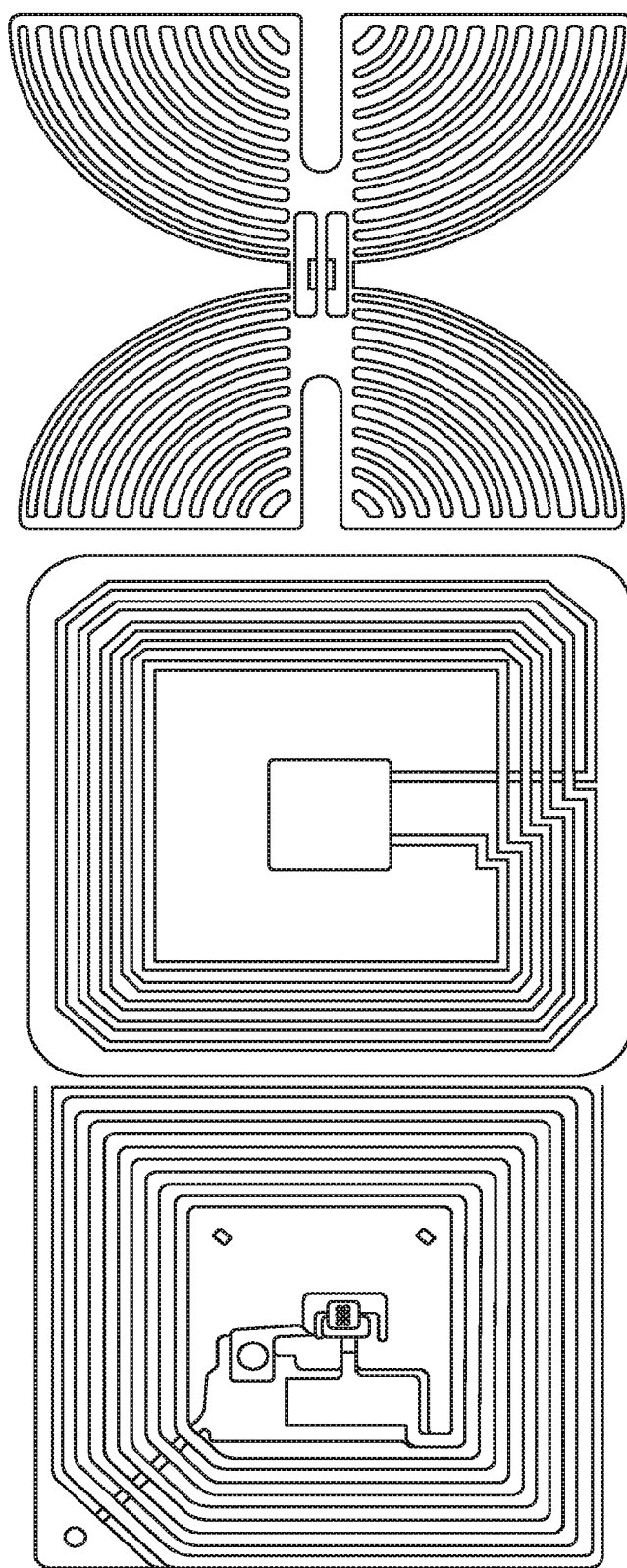
FIG. 5 shows drawings of different passive RFID tags.
Figure 11:
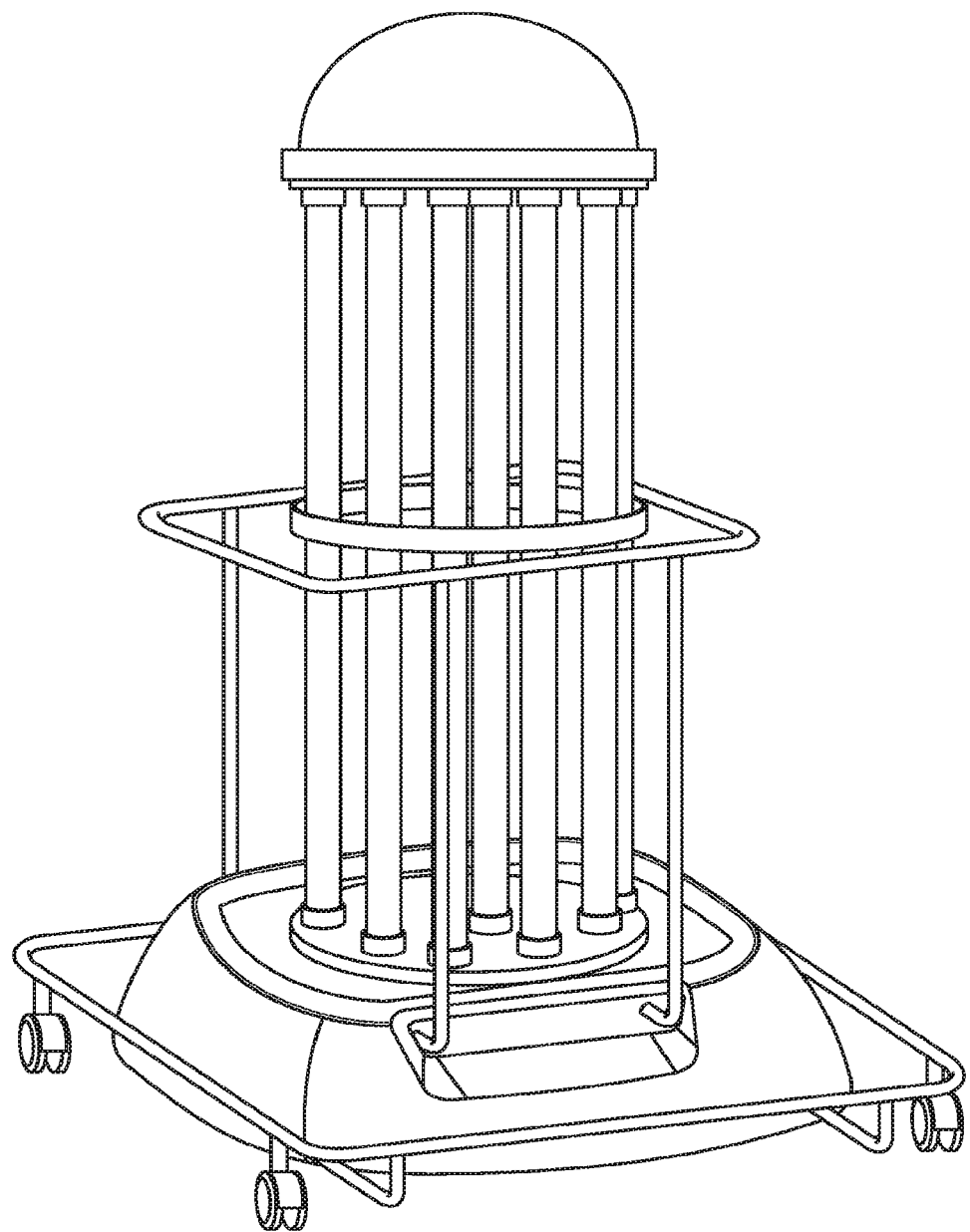
FIG. 11 shows drawing of Tru-D, a mercury-based UV device.

In one embodiment of the invention, suitable RFID tags may include passive RFIDs as shown in FIG. 5. In a further embodiment, active RFID tags, for example, as shown in FIG. 11 may be used (Supply Insight Co., Intermec Co., AeroScout or AiRISTA). The RFID with display could be of many varieties. In one embodiment, the active RFID tag may include one LED light or 2 LED lights or 2 LED lights of different colors (US Publication No. US 2010/0171586). In another embodiment, the active RFID with display may be active RFID combined with E-ink technology (U.S. Pat. No. 7,791,489). In yet another embodiment, the active RFID tag may use a technology to conserve battery of the RFID tag (U.S. Pat. No. 8,416,072). In yet another embodiment, the active RFID with display may also have a beeping device similar to the 433 MHz RFID Domino Tag Active 124010 by GAO RFID Inc.

The invention also provides methods for organizing (manually or through automated means) the disinfection of a designated area(s) contaminated with biological agent(s) comprising attaching one or more radio-frequency ID (RFID) tags to a designated area to be disinfected. The method further comprises exposing the designated area or portion thereof to a disinfecting means for a period sufficient to disinfect the designated area. Further, the method comprises obtaining a signal from the tagged designated area when disinfection is complete thereby organizing the disinfection of the designated space.

In one embodiment, the designated area(s) contaminated with biological agent(s) may be disinfected by the method of the invention.

The invention also provides methods for organizing (manually or through automated means) the process of disinfection of a designated area(s) contaminated with biological agent(s) comprising exposing the designated area or portion thereof having one or more RFID tags to a disinfecting means for a period sufficient to disinfect the designated area. The method further comprises obtaining a signal from the tagged designated area or portion thereof when disinfection is complete.

In one embodiment, the method for organizing the disinfection of a designated space contaminated with biological agent(s) may be an automated method.

In accordance with the practice of the invention, the space or room to be cleaned may be coated with a reflective coating of paint (UVC 360, Lumacept, TN). This coating enhances reflectivity of the UVC thus improving the overall disinfection and thoroughness of disinfection.

Additionally, the designated space to be disinfected may be a room or portion thereof. The room may be enclosed or open. For example, the room may be a hospital room (for humans and veterinary animals). In yet another example, the room may be in a day care center or nursery or school.

In one embodiment, the disinfecting means may be an ultra-violet light or hydrogen peroxide system as mentioned previously.

In various embodiments, the micro-organism or biological contaminant may be as mentioned previously.

In various embodiments, the RFID tag may communicate with the disinfection means. In another embodiment, the RFID tag may communicate the initiation or completion of the cleaning or disinfection cycle to a computer or data warehouse. In a further embodiment, the method comprises processing the signal from the tagged designated area to create a log of the cleaning or disinfecting history of each RFID tagged item through a computer. In yet another embodiment, comprising processing the signal from the tagged designated space or portion thereof to create a log of the cleaning or disinfecting history of each RFID tagged item through a computer. In yet another embodiment, the RFID tag permits the creation of a log of the cleaning or disinfecting history of each RFID tagged space or patient room or reusable medical equipment through a computer or data warehouse.

In another embodiment, the RFID tag may be attached to a patient or located in a patient room or unclean piece of equipment and resets the status of the designated space for future disinfection. In another embodiment, the disinfection means may communicate with multiple RFID tags and automatically cleans the entire room.

In an embodiment of the invention, the RFID tag(s) in the designated area may be passive. In another embodiment, the RFID tag(s) in the designated area are active.

The advantage of the invention includes the
- ability to keep track of clean and dirty equipment log;
- ability to distinguish clean and dirty equipment at the end user level with or without having to manually scan equipment;
- ability to prevent errors by introducing various safety mechanisms like alarms if equipment that is not clean is going to be used;
- ability to communicate with the environmental services personnel on a real time basis;
- ability for the hospital management and infection prevention and control teams to keep track of cleaning processes on a real time basis, for both equipment and patient rooms; and/or
- provides complete automation of the process thus preventing or reducing medical errors that can be fatal.

The following examples are provided to further illustrate aspects of the invention. These examples are non-limiting and should not be construed as limiting any aspect of the invention.

EXAMPLES

Example 1

For example, patient X is admitted to the hospital and is in Room A. Patient X has MRSA and has spent 5 days in Room A. During the course of his/her hospitalization, patient X touches several surfaces in Room A and also requires IV antibiotics which are delivered by an IV pump attached to an IV pole. Patient X is ready for discharge on day 5. This information is electronically entered in the hospital medical records. This electronic entry updates the housekeeping database alerting the environmental services personnel that Room A will soon be ready for cleaning. Once patient X has left the hospital, the software on the Jangama's display unit or Jangama integrated into a no-touch device such as Xenex or Bioquell displays that Room A is now available for cleaning. The environmental services personnel are alerted, and one then takes the no-touch device with/without Jangama (depending whether Jangama is integrated or standalone) to Room A for cleaning. Room A is tagged with an active RFID tag, which updates the time of entry of device for cleaning. Once cleaning of Room A is in progress, the hospital bed database indicates the same. Once room A is terminally cleaned per protocol and the no-touch device is taken out of the room, the room RFID tag updates the hospital bed database regarding the availability of that room. This interrogation upon entry and exit is provided by the RFID reader in the Jangama or no-touch device with Jangama incorporated within it. The bed management system may further have several disinfection positions that need to be completed before the room is marked as completely disinfected for certain type of disinfection systems; e.g., the Xenex device has three to four positions and the Tru-D has two positions. Merely by way of example, the disinfecting means may be arranged as follows: one for a bathroom, two in living rooms (one on either side of the bed) and one in an anteroom, if present. The bed management system shows the progress on the display as each position is completed.

Figure 6:
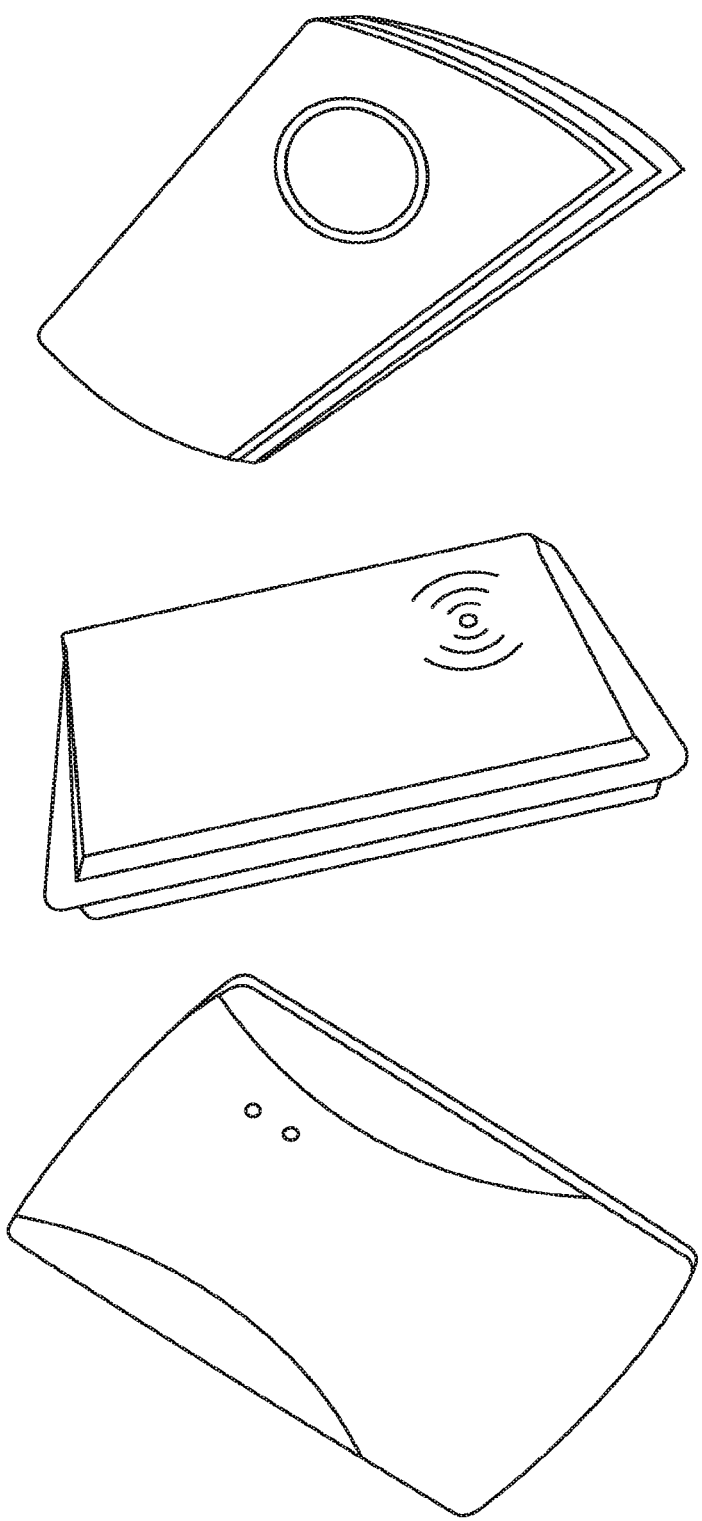
FIG. 6 shows drawings of different RFID readers.

A protocol for disinfecting medical equipment and obtaining a signal that disinfection is complete is as follows:
1. Medical equipment of interest may be tagged with a unique identifier. Examples of suitable identifiers include: RFID tag or tags (active, passive or combined), or RFID equivalents like: RTLS tags, Bluetooth ID, Wi-Fi tags, near field communication technologies or infrared tags. Active RFID tags may include LED display technology or E-ink display technology.
2. The tagged equipment may be able to communicate with both a mobile RFID reader(s) and/or fixed RFID reader(s) as shown in FIGS. 5 and 6, each of which in turn may communicate with a central data warehouse (management system). The mobile and the fixed RFID reader(s) may also have the capacity to communicate with each other. A facility's existing Wi-Fi technology may be used to enable such communications.
3. Equipment holding rooms may have a fixed RFID reader.
4. Each UV device or equivalent device of interest may incorporate a mobile RFID reader in the form of an incorporated Jangama or standalone Jangama (FIG. 9).
5. This uniquely tagged RME may have a communication range of 20-30 feet with a mobile RFID reader and a range of e.g. 4-6 feet for the fixed reader.
6. The mobile reader may also have the capacity to transmit or emit signals back to the RFID tagged RME. It also may have storage and display capacity.

7. The fixed readers may also have the capacity to transmit or emit signals back to the RFID tagged equipment.
8. The portable reader/transmitter/storage/display device (Jangama) may have many functions:
   a. Receive and recognize each of these uniquely tagged ID equipment;
   b. Ability to measure UV radiation around it or Hydrogen peroxide levels around it;
   c. Ability to send signals to the uniquely tagged equipment while in the vicinity of e.g. 4-6 feet;
   d. Ability to communicate with fixed reader/transmitter;
   e. Ability to communicate with management systems (data warehouse);
   f. Ability to store information in its hardware to later transmit to the management system in case there are Wi-Fi issues; and/or
   g. Ability to display live information about bed management as well as the ability to identify unclean equipment in the vicinity (e.g., about 20-30 feet).
9. The fixed sensor/emitter may have these functions:
   a. Receive and recognize each uniquely tagged RME within the room, at entry and exit (choke holder);
   b. Communicate with the RME being removed from/ brought in the holding area, and changing the signal on the RME appropriately;
   c. Communicate with the mobile reader; and/or
   d. Communicate with management to provide a real time feed about equipment cleaning necessity.
10. The tagged equipment may have a receiver for a unique signal. Once the unique signal is received it may display e.g. a green light and or display the word "CLEAN". The signal may be valid for 24 hours but may be customizable, for example, up to 72 hrs.
11. The tagged RME may return to unclean or red display representing unclean in the following exemplary scenarios:
    a. No unique signal from mobile reader/transmitter or fixed reader/transmitter;
    b. 24 hours have elapsed since the last signal (automatically change status to either red light or display "Unclean" at the end of 24 hours or the customized time);
    c. The equipment leaves a designated area (i.e., holding area); and/or
    d. The equipment was not within 4-6 feet of the UV unit or in the case of Hydrogen peroxide within the contained room.
12. The room itself may be lined with unique aluminum screen with panels at 45 degrees (FIG. 2) or coated with UV reflective paint. The aluminum and paint are great reflectors of UV light and may make the process of disinfection more effective as the equipment may be cleaned through the reflectivity of the panels or paint.
13. The mobile reader/transmitter/recorder (Jangama) may log each activity. For example, equipment #1 was in the vicinity (e.g. 4 feet) of the sensor at this time date, receives a total radiation of x units (0-5000 millijoules/cm$^2$ or other comparable units) for y time (0-300 minutes) and receives the clean signal at z time. If taken out of the area, the central database may record the last time taken out of clean area and record it and merge the data with the mobile unit. A data log may be maintained in MS Excel format or equivalent tabular format in the central data warehouse and may be printable for regulatory (Joint Commission/Center for Medicaid and Medicare Services) compliance and available on request during an inspection.
14. The central data warehouse may be equipped with appropriate software to recognize all tagged equipment, their location and searchable properties like some of the current RFID vendors. The database may also be able to locate each UV or equivalent device and be able to update device maintenance logs.
15. If unclean equipment is accidentally wheeled out of the designated home area then it may produce an auditory signal (e.g., beeping noise) for designated period of time and a visual signal (e.g., a light signal such as a red light signal) may blink for a designated time period to alert the handler that the equipment is not clean.

Figure 12:
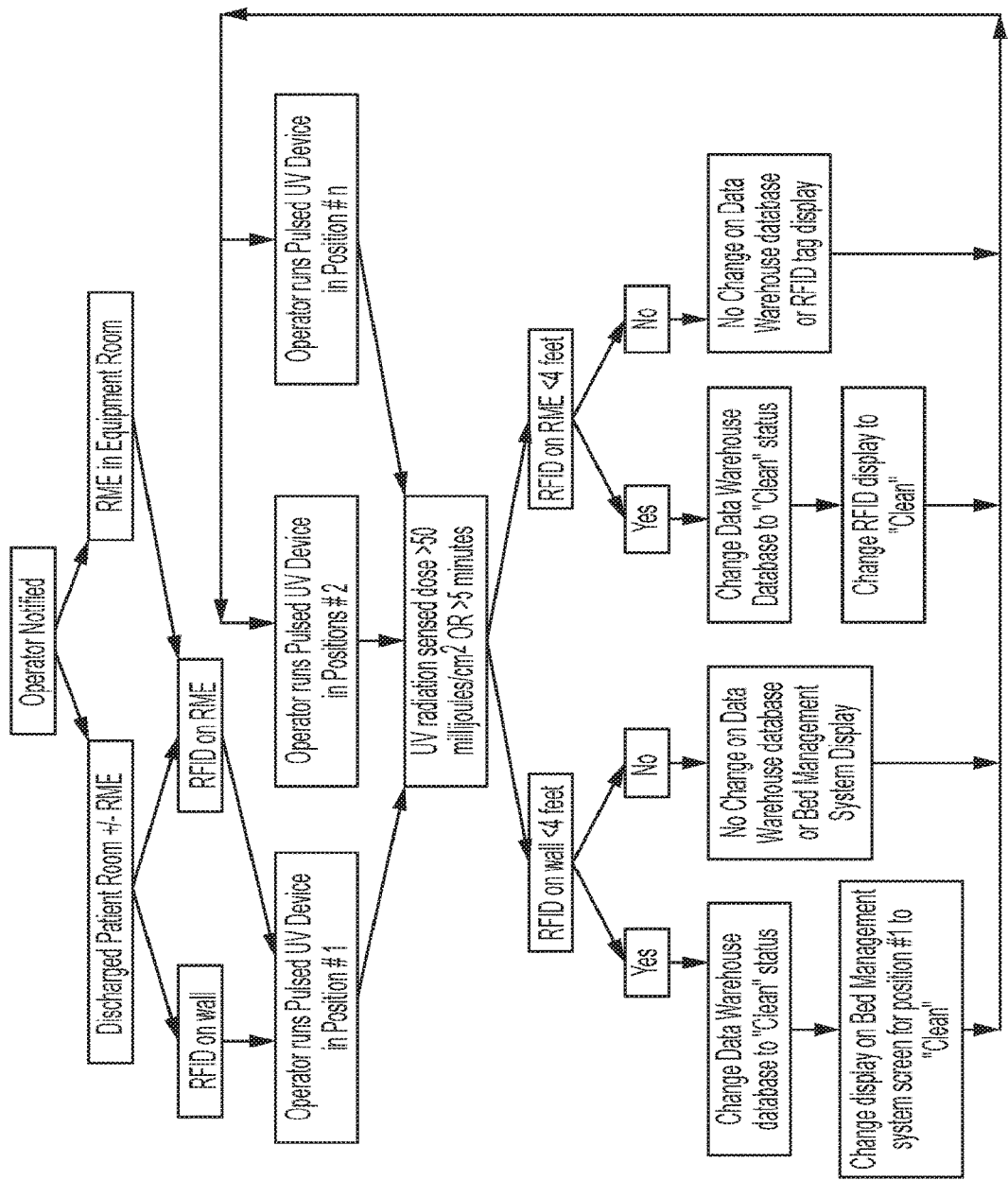
FIG. 12 shows an overall flow chart demonstrating the workings of the Jangama with an UV-based cleaning (also referred to herein as disinfecting) system.

Active Management of Clean and Unclean Inventory Using Pulsed Xenon UV Device: (FIGS. 1 and 12)

Each RFID tagged equipment is managed by a Wi-Fi or similar technology enabled central data warehouse through a fixed reader in each of the equipment holding rooms. Once the UV device equipped with the Jangama is used to clean the RME it records each uniquely tagged RME and transmits that information to the central database/Management system. This database may be updated on a real time basis, meaning, e.g., that it updates with each cleaning and each movement of the RFID tagged RME. An UV operator may be able to access this information on the UV device using the mobile reader/transmitter/storage/display unit (Jangama) on a real time basis as well, thereby alerting the operator to the holding areas in need of clean equipment. Also, if the UV device is in the vicinity of a holding area with a high volume of unclean equipment, an instant beep/message (like a text message) may alert the operator handling the device. This may help with active management of clean/unclean equipment especially near high turnover areas such as Operating Rooms. The same device may also display a feed as to where the next room needs to be cleaned. This feed may be fed to the display screen on Jangama from bed control or bed management as well as central data warehouse servers.

The mobile sensor/emitter/storage device (Jangama) may also communicate with the fixed readers and all the RMEs in disinfection range (e.g., 4-6 feet) which may be targeted for cleaning. The fixed readers as shown in FIG. 6 may change the status of these visible RME in the central database to "BEING DISINFECTED". Once the disinfection process is completed, the portable sensor of Jangama may communicate the completed cycle to the fixed readers and the database may be updated to "CLEAN" for these visible equipment and the resets the timer on the database and the tagged RME. It may be necessary to relocate the UV device to different sections of the holding room to effectively clean all the equipment (as the room may be bigger than e.g. 6×6 feet), as all equipment in need of cleaning may not be within UV range. At the pre-determined time, the fixed sensor may be able to turn off the "green signal" on all equipment that would no longer be considered clean. Alternatively, the equipment may be manually reset for cleaning. All this communication may occur over the pre-existing Wi-Fi communications available at the facility.

Figure 10:
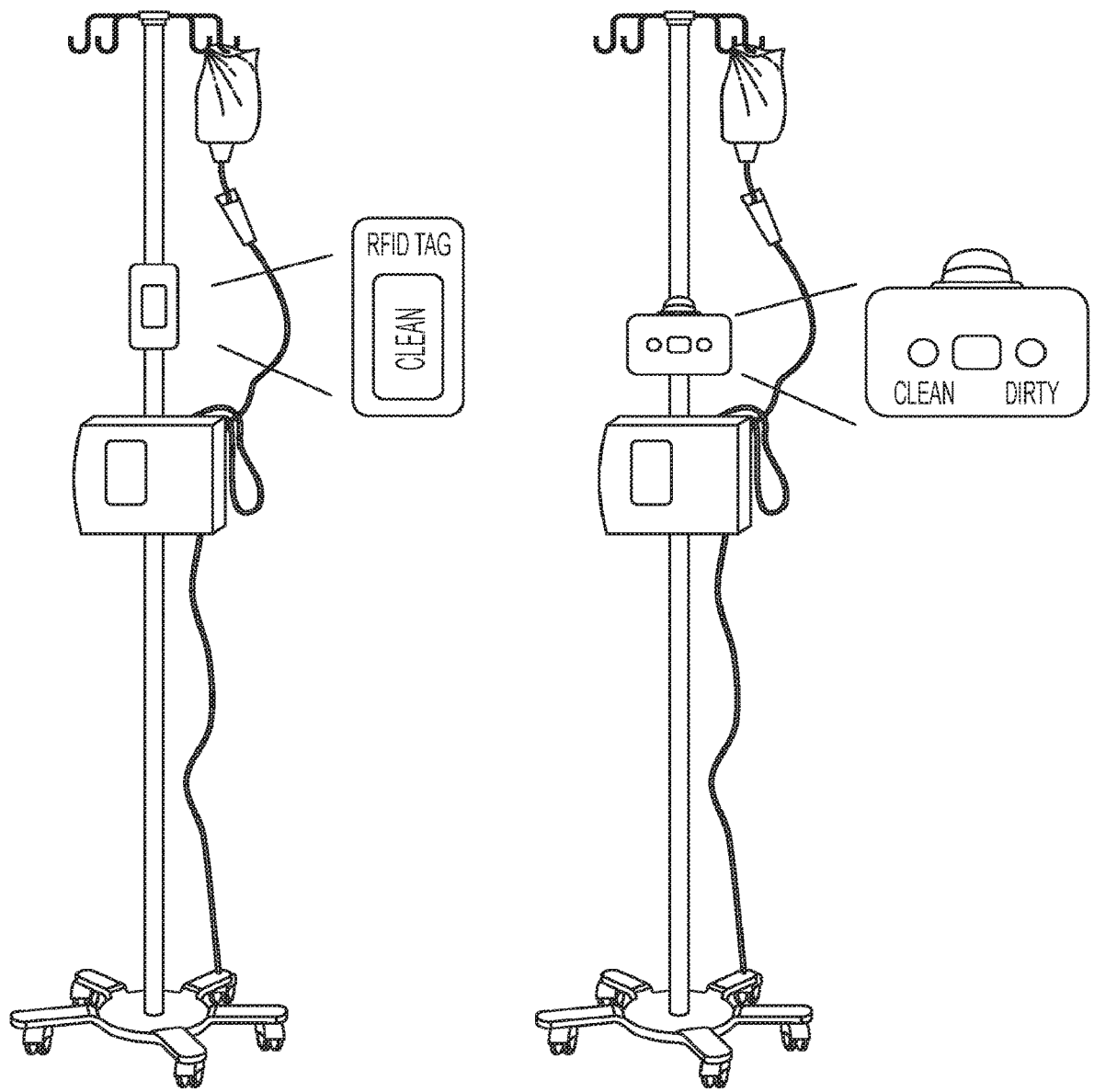
FIG. 10 shows a drawing of an IV pole tagged with active RFID tags, which depict clean versus dirty equipment status. The drawing on the left is an active RFID tag with e-ink technology; on the right, is an active RFID tag with LED display technology.

For example, if patient Y in room B needs IV fluids, the nurse may go to the utility/equipment storage room to get an IV pole that can be used for patient Y. All IV poles stored in the storage room have active RFID tags which illuminate "GREEN" for clean and "RED" for unclean as shown in FIG. 10. The storage room entrance/exit area has an active RFID reader. The nurse takes an IV pole which has the "RED" illuminated on it, but fails to notice it. As this IV pole is taken out of the utility room, the RFID reader interrogates the RFID tag on the IV pole and sounds out an alarm that an unclean pole is being taken out of the room. Should the "GREEN" illuminated pole be taken, no alarm will sound. The active tag on the IV pole now is in use in room B, which will result in software update of its exact location.

In another example, patient Y in room B needs IV fluids. The nurse goes to the utility/equipment storage room to get an IV pole that can be used for patient Y. All IV poles stored in the storage room have active RFID tags which display "Clean" and "Dirty" on an E-ink-based RFID tag as shown in FIG. 10. The storage room entrance/exit area has an active RFID reader. The nurse takes an IV pole which has the word "DIRTY" displayed on it, but fails to notice it. As this IV pole is taken out of the utility room, the RFID reader interrogates the RFID tag on the IV pole and sounds out an alarm indicating that an unclean pole is being taken out of the room. Should a "Clean" displayed pole be taken, no alarm will sound. The active tag on the IV pole now is in use in room B, which will result in a software update of its exact location.

The fixed readers have ability to receive signals from 2 sources. One from fixed RFID reader or Blue tooth device and the other from the mobile reader/transmitter (Jangama).

The fixed reader may communicate all the information with a central server/management system through the facility's Wi-Fi.

The mobile reader/transmitter (Jangama) may have the ability to communicate with RFID/Blue tooth equipment, fixed sensors, central server or management system through Wi-Fi. The received signal strength indication (RSSI) may be used to determine which room the equipment is in.

Real Time Location Systems (RTLS)

Real Time Location Systems (RTLS) are used to determine the physical proximity of active RFID tags and can be used in conjunction with this invention. This can be accomplished by installing fixed RFID readers at strategic locations where the active tag can be read simultaneously by two or more readers. Pre-determined algorithms can then determine the exact location of the active RFID tags by the RSSI level and triangulation. This would determine an approximate location within e.g. about 10 feet depending on the number of reader access points are used. For further accuracy, additional sensor technologies may be incorporated into the tag such as ultra-sound or infra-red.

Components

1. RFID tag or equivalent for each equipment that needs to be tracked and disinfected;
2. Mobile sensor/reader/signal emitter/storage device/display device (Jangama);
3. Clean/Unclean displayer;
4. Green/Red light displayer;
5. Beeper/this device is "unclean" announcer;
6. UV Reflectors/paint in the room;
7. Room readers;
8. Data warehouse master database/Management system.

Example 2

Another way to communicate with the RFID tagged RME may be through a no-touch disinfection (NTD) remote control mechanism where after the NTD device is done disinfecting, the NTD device sends a signal to the RFID tag and turns on a visual display (e.g., a LED light having a green color. In contrast, the default light signal may be a different color, such as red. The greed and red light can illuminate Clean and Unclean, respectively as displayed below. The lights may be enclosed behind these wordings in a square box with these wording on the front and LED lights behind them. It may also display the words clean or dirty using the E-ink technology.

The mobile continuous RFID reader mobile display (Jangama) and the tagged equipment may communicate with each other within e.g. 20-30 feet vicinity on a real time basis. Another mobile reader may be activated just like the light after UV radiation for 2 seconds. It may identify and transmit all the equipment ID for e.g. about less than 4 feet range and communicate that information to the management system to verify the equipment status as clean or dirty.

At chokepoints, a reader may be connected to the same mechanism that turns the light off or turns it red if it moves outside of the chokepoint area. The off mechanism (or turning it red/unclean) is triggered by the reader and the reader sends a message to the management system to change the log status as moved and now unclean. The same reader may have a voice alert/beep when unclean equipment is moved from the holding area away from chokepoint. Similarly, all the above information may display on E-ink based RFID tags.

Example 3

The following is a description of a process for creating status updates using the RFID tagged system of the invention.

Process

1. The designated rooms will have unique identifiers: RFID tags (active, passive or combined), or RFID equivalents like: RTLS tags, Bluetooth ID, Wi-Fi tags, near field communication technologies or infrared tags. The number of tags may range from 2-3 (with at least one in the main room and 1 in the bathroom). The exact number of tags in each room will vary depending on the size of the room. For example, a room that is bigger than 6×6 feet may have at least 2 tags. Also, the central database management or bed management may have the information of number of tags and their locations (positions) in each room.

2. The portable sensor/emitter/storage (Jangama) may have 3 functions:
   a. Receive and recognize each of these unique tagged ID rooms.
   b. Ability to measure UV light amount/exposure around it or Hydrogen peroxide levels around it.
   c. A RFID reader may send a signal back to bed management system; via the existing facility's Wi-Fi; once the disinfection cycle is completed, thereby indicating the area that has been recently disinfected; on a real time basis.

3. The mobile sensor (Jangama) may not recognize the RFID tags, which are not within e.g., 4-6 feet of the UV unit or in the case of Hydrogen peroxide within the contained room.

4. The portable sensor/emitter/recorder (Jangama) may log each of the activity. For example, that room #1 east wall was in the vicinity (about 4 feet) of the sensor at A time/date, may have received a total radiation of X many units for Y length of time, may have received the clean signal at Z time; room #1 west wall was in vicinity (about 4 feet) of the sensor at B time/date, may have received a total radiation of X many units for Y length of time, may have received the clean signal at Z time; room #1 bathroom was in vicinity (about 4 feet) of the sensor at C time/date, may have received a total radiation of X many units for Y length of time, may have received the clean signal at Z time. Combined data log may be maintained in Excel format or tabular format so it is printable and can be showed to regulatory authorities (JC/CMS) on request or during inspection.

5. Once room #1 is thoroughly disinfected, the mobile sensor (e.g., including a Jangama) may update the central database/bed management system and display that particular room as "clean" for bed management and log when all the areas of the room are cleaned (it may remain in "Unclean" status if the EMS person missed a position for UV disinfection devices like Xenex).

6. Once that particular room is assigned to a patient through bed management, the room may be displayed as "Occupied".

7. Once the status of an Occupied room in changed to Unoccupied/discharged in bed management, the mobile sensor (Jangama) log may add the particular room to its "To be Cleaned" database, alerting the operator to rooms in need of cleaning. Alternatively, the status of a patient room may be reset to "To be Cleaned" manually or after a predetermined time.

Example 4

The "Jangama" may have the following components (FIG. 9):
1. RFID reader
2. RFID Controller
3. Display panel/unit
4. Wi-Fi network integrator (transmitter/receiver)
5. Microprocessor
6. Sensor signal processor
7. Sensors
8. Antennas
9. Memory The Jangama can be integrated into an existing no-touch disinfection device circuit board instead of a stand-alone device.

Break down of the communication that occurs between different components of the system: The RFID reader or interrogator or controller could be the same unit. The reader/interrogator reads and retrieves information, whereas the controller can send a signal back to RFID tag to rewrite memory or change display settings.

1. Communication Between the RFID Reader & Active Tag:

The RFID Reader sends an enquiry which is received by a RFID tag. Active RFID tags store memory values corresponding to clean or dirty that are accessed by the reader. At the same time, each RFID tags unique ID is also accessed. This information is transmitted from the RFID reader to the mobile unit as well as the data warehouse through a Wi-Fi or wired network.

2. Communication Between the RFID Controller and Active Tag:

The controller sends an enquiry to a RFID tag, which replies to the controller the currently stored memory value (corresponding to clean or dirty) along with the unique ID for the tag. This information is also relayed to the microprocessor which in turn communicates with the stored information in the data warehouse through the existing Wi-Fi system.

Once the condition for disinfection is satisfied, the microprocessor asks the controller to issue a clean signal back to the active RFID tag and change the memory value to clean. The signal will only be used to active RFID tags within a set distance parameter of 4 feet, but this could also be anywhere from 0-8 feet. The controller confirms the RFID tags unique ID/new memory value and sends it back to the processor. The microprocessor then relays the new values to the data warehouse to clean status for those RFID tags which were in the set distance parameter with a time and date stamp.

Figure 7:
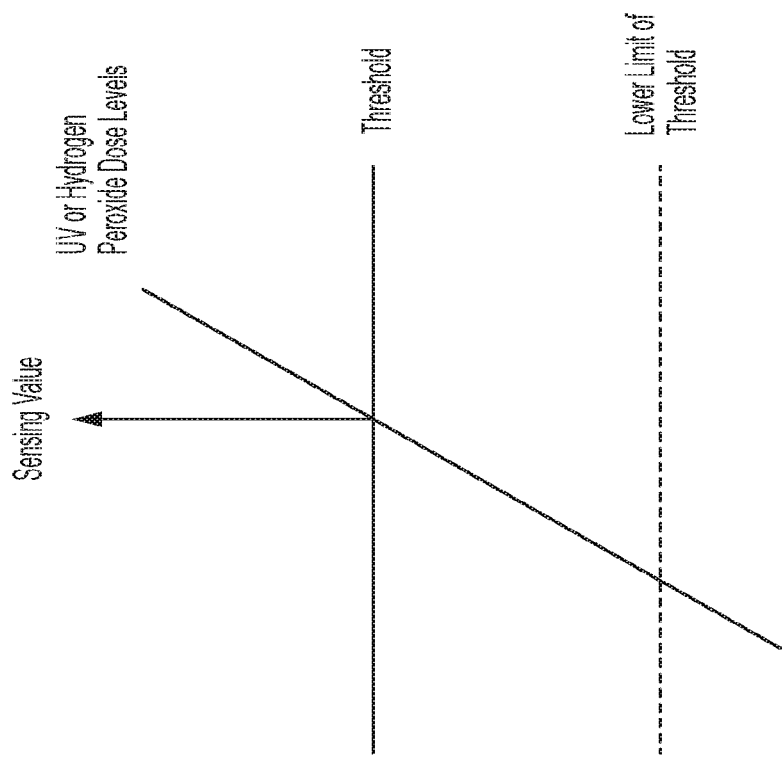
FIG. 7 shows graphs of threshold sensing values over time.
Figure 7:
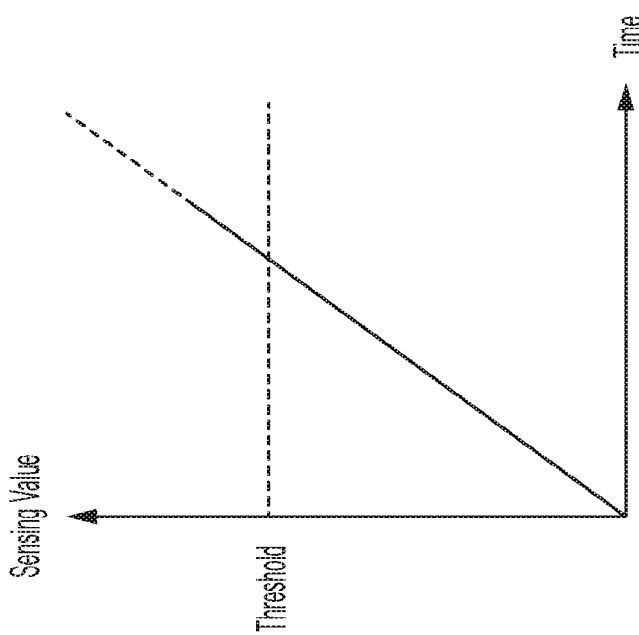

3. Communication Between Sensor Signal Processor and Sensors:

Sensors can sense various external parameters like UV, Hydrogen peroxide. Once a certain upper limit threshold is reached in the sensor (10-500 millijoules/cm$^2$ for UV or 10-20000 ppm for hydrogen peroxide), it sends a signal to the sensor signal processor, which changes they signal to a digital numerical signal for the microprocessor to know that certain values have been met (FIG. 7). This is referenced to the stored upper threshold limit for that sensor. If above the threshold, the microprocessor asks the RFID controller to issue a clean signal to the active RFID tags in a certain distance parameter as described above.

4. Sensors:

The sensors can sense various parameters like temperature, pressure, mercury based UV dose (continuous), pulsed xenon UV dose (cumulative dose of all pulses in a set time), or hydrogen peroxide concentration. The sensors transmit the sensed dose to the sensor signal processor.

5. Sensor Signal Processor:

The function of the sensor signal processor is to take the sensor input, convert it to a digital signal and reference it to the stored reference parameters for various external effects like UV or Hydrogen peroxide. Once the threshold is reached, the sensor signal processor will continue to send a signal of condition being met to the microprocessor for next 60 seconds or until the sensor keeps sending the signals whichever is later. For those 60 seconds, the sensor value will be set as met, even if the sensors sense no additional UV or H2O2. After 60 seconds, the parameters will be set to below threshold until another sensing event happens (FIG. 7). The sensor value could be set as met, for example, anywhere from 30 seconds to 300 seconds.

In yet another example, the sensors and sensor signal processors may be optional, when time is used as a parameter to fulfill condition being met algorithm for the RFID controller to transmit a signal to nearby RFID tags. This is usually possible if the circuit board is integrated into a no-touch disinfection system such as Pulsed UV or Mercury based UV or Hydrogen peroxide systems thus eliminating the need to sense an external signal.

6. Display Unit:

The display unit will have the capacity to display various things similar to a notebook or tablet. It can display information newly created in the microprocessor or the live information it receives from the data warehouse servers through Wi-Fi or live bed management feed through the bed management servers. It can also display information about any dirty RME in the near vicinity of the mobile unit. It can also perform other functions of a display unit like other tablets or phones receiving text or video chat again through a Wi-Fi network or a cellular network.

7. Microprocessor:

The microprocessor is like the brain of Jangama. Its functions as a central processing unit for all external signals and is also the origin of digital signal either generated intrinsically or with the help of algorithms in the data warehouse. The digital signals are then relayed to RFID interrogator or controller for their actions to follow. Digital signals that originate from the microprocessor are continuously fed to the data warehouse for determining the location or position of a RFID tagged device much like a mobile RFID interrogator. Similarly, the microprocessor has the ability to process the data warehouse algorithms and convert them to RFID signals through controller and interrogator to read or write a RFID tag or change the memory in a RFID tag to change the clean or dirty labeling on the RFID tags that met the condition. In another example, the microprocessor may take the form of a FPGA (Field-Programmable Gate Array), ASIC (Application-Specific Integrated Circuit), or some other form of integrated analog or digital logic gates.

7. Data Warehouse:

The data warehouse houses all the information required to function. Certain new algorithms will need to be incorporated into existing real time location services algorithms. A new algorithm to match the sensor values, distance, exposure time and choke point integration will be added. Alternatively, these algorithms may be incorporated into the devices themselves.

8. The Active RFID with Display:

The RFID with display could be of many varieties as previously described in the detailed description.

9. Memory:

The memory component is optional and will mainly interact with the microprocessor and store data for a limited period of time. It is crucial to have data stored in this backup memory in case there are transmission issues with the facility Wi-Fi. Data could be stored until a proper Wi-Fi connection is established or until the unit can be manually synced with the central data warehouse.

Example 5

In another embodiment the invention would be used in conjunction with choke points. If tagged equipment is allowed to move from one area to another area after it has been designated as clean, or if clean equipment moves from one patient to another patient room for example, this may lead to cross contamination. To prevent this, the data warehouse will include a choke point algorithm.

For example, a piece of clean equipment is taken out of a current patient room as it was not being used. Doing so carries the risk of cross contamination. To prevent this, each patient room will have a choke point, where an active reader will sense the movement of the tagged equipment beyond a certain point and send a signal to the data warehouse, which confirms the equipment movement out an area and that it should not have been moved. The data warehouse will send a signal back to the controller at the choke point to change the RFID memory to dirty as soon as the choke point is breached. It will also sound an alarm to the end user about the equipment being dirty now. Such algorithms already exist in, for example, Avante's RFID "Access-Trakker," but such algorithms need to be modified to accommodate current aspects of invention as related to clean and dirty equipment. Integration of such concept will improve patient safety and prevent medical errors.

Similarly clean equipment could be in a clean equipment room. If the clean equipment were to travel outside the clean equipment room, the reader at the choke point will send a signal to the data warehouse that the clean equipment was removed from the clean equipment room. The data warehouses algorithm will track this equipment's movements for next 5 minutes. If the equipment enters another patient room, then the readers at the patient rooms' choke point will note this entry. Once this equipment enters the patient room, the data warehouse will change the entry to dirty and should the equipment be taken out again beyond the patient room's choke point, a similar process as described above will happen.

Similarly in the clean equipment room, if dirty equipment is being placed back in the room, the choke point reader will confirm with the data warehouse of the equipment's dirty status, record the movement and change the display on equipment to unclean, and beep the equipment handling person that the equipment is unclean.

Various such algorithms will be built to track the equipment at various stages of its movement alerting the end user both visually as well as by noise about the current status of the equipment.

Example 6

The following are algorithms that may be used in conjunction with the Jangama invention:

Algorithm 1: UV dose fulfillment algorithm
1. Operator starts UV disinfection device
2. Sensor starting sensing UV and calculates the cumulative dose of UV
3. Once UV dose exceeds 100 milliwatts/$cm^2$ or millijoules/$cm^2$ then required dose for disinfection is fulfilled.

Algorithm 2: Hydrogen peroxide fulfillment algorithm:
1. Operator starts hydrogen peroxide disinfection device
2. Sensor starting sensing hydrogen peroxide and calculates the cumulative dose of hydrogen peroxide.
3. Once hydrogen peroxide dose exceeds 2000 parts per million (ppm) then required dose for disinfection is fulfilled. The ppm range is 2-20,000 as it varies on the size of the room.

Algorithm 3: Dirty to Clean Display Change Algorithm
1. Once UV dose criteria is fulfilled the RFID controller will send a back to the RFID tags memory and it will change the stored value that represents "dirty" to stored value for memory that represents "clean".

REFERENCES

1. Rutala W A, Weber D J. Are Room Decontamination Units Needed to Prevent Transmission of Environmental Pathogens? Infect Control Hosp Epidemiol. 2011 August; 32 (8): 743-747.
2. ParVez N, Jinadatha C, Fader R, et al. Universal MRSA Nasal Surveillance: Characterization of Outcomes at a Tertiary Care Center and Implications for Infection Control. Southern Medical Journal, Volume 103, Number 11, November 2010.
3. Otter J A, Yezli S, French G L. The role played by contaminated surfaces in the transmission of nosocomial pathogens. ICHE 2011 July; 32 (7):687-699.
4. Boyce J M, Havill N L, Moore B A. Terminal Decontamination of Patient Rooms Using an Automated UV Light. ICHE, 2011; 32 (8):737-742.

5. Morgan D J, Rogawski E, Thom K A, et al. Transfer of multidrug-resistant bacteria to healthcare workers' gloves and gowns after patient contact increases with environmental contamination. Crit Care Med. 2012 April; 40 (4):1045-51. PubMed PMID: 22202707.
6. Datta R, Platt R, Yokoe D S, et al. Environmental cleaning intervention and risk of acquiring multidrug-resistant organisms from prior room occupants. Arch Intern Med. 2011 Mar. 28; 171 (6):491-4. PubMed PMID: 21444840.
7. Zaidi M, Angulo M, Sifuentes-Osornio J. Disinfection and sterilization practices in Mexico. J. Hosp. Infect. 1995; 31:25-32.
8. McCarthy G M, Koval J J, John M A, et al. Infection control practices across Canada: do dentists follow the recommendations? J. Can. Dent, Assoc. 1999; 65:506-11.
9. Spach D H, Silverstein F E, Stamm W E. Transmission of infection by gastrointestinal endoscopy and bronchoscopy. Ann. Intern. Med. 1993; 118:117-28.
10. Weber D J, Rutala W A. Lessons from outbreaks associated with bronchoscopy. Infect. Control Hosp. Epidemiol. 2001; 22:403-8.
11. Weber D J, Rutala W A, DiMarino A J, Jr. The prevention of infection following gastrointestinal endoscopy: the importance of prophylaxis and reprocessing. In: DiMarino A J, Jr, Benjamin S B, eds. Gastrointestinal diseases: an endoscopic approach. Thorofare, N.J.: Slack Inc., 2002: 87-106.
12. Meyers H, Brown-Elliott B A, Moore D, et al. An outbreak of *Mycobacterium chelonae* infection following liposuction. Clin. Infect. Dis. 2002; 34:1500-7.
13. Lowry P W, Jarvis W R, Oberle A D, et al. *Mycobacterium chelonae* causing otitis media in an ear-nose-and-throat practice. N. Engl. J. Med. 1988; 319:978-82.
14. Centers for Disease Control and Prevention. *Pseudomonas aeruginosa* infections associated with transrectal ultrasound-guided prostate biopsies—Georgia, 2005. MMWR CDC Surveill. Summ. 2006; 55:776-7.
15. Mehta A C, Prakash U B S, Garland R, et al. Prevention of flexible bronchoscopy-associated infection. Chest 2006; 128:1742-55.
16. Turner F J. Hydrogen peroxide and other oxidant disinfectants. In: Block S S, ed. Disinfection, sterilization, and preservation. Philadelphia: Lea & Febiger, 1983: 240-50.
17. Carling P C, Parry M F, Von Beheren S M. Identifying opportunities to enhance environmental cleaning in 23 acute care hospitals. ICHE 2008 January; 29 (1): 1-7.
18. Rutala W A, Gergen M F, Weber D J. Room decontamination with UV radiation. Infect Control Hosp Epidemiol. 2010 October; 31 (10):1025-9.
19. Stibich M, Stachowiak J, Tanner B, et al. Evaluation of a pulsed-xenon ultraviolet room disinfection device for impact on hospital operations and microbial reduction. Infect Control Hosp Epidemiol. 2011 March; 32 (3):286-8.
20. Rutala W A, Gergen M F, Tande B M, et al. Rapid hospital room disinfection using ultraviolet (UV) light with a nanostructured UV-reflective wall coating. Infect Control Hosp Epidemiol. 2013 May; 34 (5):527-9.
21. Holmdahl T, Lanbeck P, Wullt M, et al. A Head to Head Comparison of Hydrogen Peroxide Vapor and Aerosol Room Decontamination Systems. ICHE, 2011; 32 (9): 831-836
22. Block S S. Peroxygen compounds. In: Block S S, ed. Disinfection, sterilization, and preservation. Philadelphia: Lippincott Williams & Wilkins, 2001:185-204.
23. US 20100171586 A1
24. U.S. Pat. No. 8,416,072 B2
25. US 20100295943 A1
26. U.S. Pat. No. 7,158,030 B2
27. U.S. Pat. No. 7,319,397 B2
28. U.S. Pat. No. 7,342,497
29. U.S. Pat. No. 6,696,954
30. U.S. Pat. No. 6,703,935
31. U.S. Pat. No. 6,943,688
32. U.S. Pat. No. 6,973,716
33. U.S. Pat. No. 6,665,193
34. U.S. Pat. No. 6,657,543
35. U.S. Pat. No. 6,883,710
36. U.S. Pat. No. 6,961,000
37. U.S. Pat. No. 7,036,729
38. U.S. Pat. No. 7,098,793
39. U.S. Pat. No. 7,154,046
40. U.S. Pat. No. 7,158,030
41. U.S. Pat. No. 7,319,397
42. U.S. Pat. No. 7,342,497
43. U.S. Pat. No. 7,423,535
44. U.S. Pat. No. 7,382,255
45. US 20100171586 A1
46. EP 2504822 A1

What is claimed is:

1. A device, comprising:
an ultraviolet light sensor;
a fluid sensor;
a timer; and
circuitry to activate the timer, wherein the circuitry is configured to:
start tracking a first duration upon receipt of a unique signal from the ultraviolet light sensor; and
start tracking a second duration upon receipt of a different unique signal from the fluid sensor.

2. The device of claim 1, further comprising a changeable display and other circuitry to alter the changeable display upon receipt of either the unique signal or the different unique signal.

3. The device of claim 2, wherein the other circuitry alters the changeable display to indicate a disinfection status of the device.

4. The device of claim 2, wherein the other circuitry further alters the changeable display upon the first duration or the second duration reaching a predetermined amount of time.

5. The device of claim 4, wherein the predetermined amount of time is approximately 24 hours or longer.

6. The device of claim 2, further comprising additional circuitry to alter the changeable display after receiving a movement signal that indicates movement of the device.

7. The device of claim 6, wherein the movement signal indicates the device crossing a chokepoint.

8. The device of claim 1, wherein the device is a medical device or medical equipment.

9. The device of claim 1, further comprising a wireless communication transmitter configured to send, upon receipt of either the unique signal or the different unique signal, a status signal to an external database indicating the device has been exposed to a disinfectant.

10. A system, comprising:
an ultraviolet light sensor;
a fluid sensor;
a timer; and
circuitry to activate the timer, wherein the circuitry is configured to:
start tracking a first duration upon receipt of a unique signal from the ultraviolet light sensor; and start tracking a second duration upon receipt of a different unique signal from the fluid sensor.

11. The system of claim 10, further comprising a portable apparatus configured to facilitate disinfection of a room.

12. The system of claim 11, wherein the portable apparatus comprises a chemical disinfectant source.

13. The system of claim 11, wherein the portable apparatus comprises an ultraviolet light lamp arranged to project light into an ambient of the apparatus.

14. The system of claim 11, wherein the ultraviolet light sensor, the fluid sensor, the timer and the circuitry are arranged in a device separate from the portable apparatus.

15. The system of claim 14, wherein the plurality of wireless communication tags are respectively attached to discrete medical devices and/or discrete pieces of medical equipment.

16. The system of claim 14, wherein the plurality of wireless communication tags are attached to surfaces that are fixedly arranged in a room or area.

17. The system of claim 10, further comprising a changeable display and other circuitry to alter the changeable display upon receipt of either the unique signal or the different unique signal.

18. The system of claim 10, further comprising a wireless communication transmitter configured to send, upon receipt of either the unique signal or the different unique signal, a status signal to an external database indicating disinfection is complete.

19. The system of claim 10, further comprising a plurality of wireless communication tags each having a changeable display and circuitry to alter their respective changeable display upon receipt of a disinfection status signal.

* * * * *